(12) United States Patent
Figeys et al.

(10) Patent No.: US 11,933,790 B2
(45) Date of Patent: *Mar. 19, 2024

(54) PROTEIN COMPOSITION AND METHODS FOR ANALYSING MICROBIOTA

(71) Applicant: UNIVERSITY OF OTTAWA, Ottawa (CA)

(72) Inventors: Joseph Michel Daniel Figeys, Ottawa (CA); Alain Christophe Stintzi, Ottawa (CA); David R. Mack, Ottawa (CA); Xu Zhang, Ottawa (CA); Zhibin Ning, Ottawa (CA)

(73) Assignee: UNIVERSITY OF OTTAWA, Ottawa (CA)

( * ) Notice: Subject to any disclaimer, the term of this patent is extended or adjusted under 35 U.S.C. 154(b) by 397 days.

This patent is subject to a terminal disclaimer.

(21) Appl. No.: 17/159,731

(22) Filed: Jan. 27, 2021

(65) Prior Publication Data

US 2021/0255197 A1    Aug. 19, 2021

Related U.S. Application Data

(63) Continuation of application No. 16/305,461, filed as application No. PCT/CA2017/050666 on Jun. 1, 2017, now Pat. No. 11,175,294.

(60) Provisional application No. 62/344,247, filed on Jun. 1, 2016.

(51) Int. Cl.
| | |
|---|---|
| *G01N 33/68* | (2006.01) |
| *A61B 5/00* | (2006.01) |
| *C12Q 1/16* | (2006.01) |
| *G01N 33/50* | (2006.01) |
| *G16B 30/10* | (2019.01) |
| *G16B 40/10* | (2019.01) |
| *G16B 40/20* | (2019.01) |
| *G16H 50/20* | (2018.01) |
| *G16H 50/30* | (2018.01) |
| *G16H 50/70* | (2018.01) |

(52) U.S. Cl.
CPC ....... *G01N 33/6848* (2013.01); *A61B 5/4255* (2013.01); *C12Q 1/16* (2013.01); *G01N 33/5023* (2013.01); *G01N 33/5091* (2013.01); *G16B 30/10* (2019.02); *G16B 40/10* (2019.02); *G16B 40/20* (2019.02); *G16H 50/20* (2018.01); *G16H 50/30* (2018.01); *G16H 50/70* (2018.01); *A61B 2503/42* (2013.01); *G01N 2223/01* (2013.01); *G01N 2570/00* (2013.01); *G01N 2800/06* (2013.01)

(58) Field of Classification Search
CPC ........... G01N 33/6848; G01N 33/5023; G01N 33/5091; G01N 2223/01; G01N 2570/00; G01N 2800/06; A61B 5/4255; A61B 2503/42; C12Q 1/16; C12Q 1/04; G16B 30/10; G16B 40/10; G16B 40/20; G16H 50/20; G16H 50/30; G16H 50/70; Y02A 90/10; C40B 50/06
See application file for complete search history.

(56) References Cited

U.S. PATENT DOCUMENTS

| | | |
|---|---|---|
| 11,175,294 B2 | 11/2021 | Figeys et al. |
| 2019/0331693 A1 | 10/2019 | Figeys et al. |

FOREIGN PATENT DOCUMENTS

| | | |
|---|---|---|
| CN | 101782581 A | 7/2010 |
| CN | 102796682 A | 11/2012 |
| WO | WO-2012170478 A1 | 12/2012 |
| WO | WO-2012170711 A1 | 12/2012 |
| WO | WO-2017205981 A1 | 12/2017 |

OTHER PUBLICATIONS

Pan, C., et al., "Quantitative Tracking of Isotope Flows in Proteomes of Microbial Communities," *Molecular & Cellular Proteomics* 10(4):M110.006049, American Society for Biochemistry and Molecular Biology, United States (Apr. 2011).
Arsene-Ploetze, F., et al., "Proteomic tools to decipher microbial community structure and functioning," *Environmental Science and Pollution Research International* 22(18):13599-13612, Springer, Germany (published online Dec. 2014).
International Preliminary Report on Patentability for International Application No. PCT/CA2017/050666, The International Bureau of WIPO, Switzerland, dated Dec. 4, 2018, 7 pages (replaced).
International Search Report for International Application No. PCT/CA2017/050666, Canadian Intellectual Property Office, Canada, dated Sep. 18, 2017, 3 pages.
CIPO Examination Notes, Search Strategy for International Application No. PCT/CA2017/050666, dated Dec. 7, 2017, 2 pages.
International Preliminary Report on Patentability for International Application No. PCT/CA2017/050666, The International Bureau of WIPO, Switzerland, dated Jan. 29, 2019, 7 pages (corrected version).
Written Opinion for International Application No. PCT/CA2017/050666, Canadian Intellectual Property Office, Canada, dated Jan. 24, 2019, 6 pages (corrected version).

(Continued)

*Primary Examiner* — David W Berke-Schlessel
*Assistant Examiner* — Susan E. Fernandez
(74) *Attorney, Agent, or Firm* — Sterne, Kessler, Goldstein & Fox P.L.L.C.

(57) ABSTRACT

A method of isotope-labelling a microbiota sample. It involves providing a first microbiota sample that was obtained from a given source; exposing the first microbiota sample to an isotope enriched medium; and culturing the exposed first microbiota sample in the isotope enriched medium to obtain an isotope-labelled microbiota sample, wherein the isotope labelled metaproteome of the isotope-labelled microbiota sample is taxon specific for taxa present in the first microbiota sample when initially obtained from the given source.

13 Claims, 17 Drawing Sheets

(56) References Cited

OTHER PUBLICATIONS

Written Opinion for International Application No. PCT/CA2017/050666, Canadian Intellectual Property Office, Canada, dated Sep. 18, 2017, 6 pages (replaced).
Supplementary European Search Report for EP Application No. EP 17 80 5452, The Hague, Netherlands, dated Feb. 11, 2020, 3 pages.
Chauhan, A., and Jain, R. K., "Biodegradation: Gaining insight through proteomics," *Biodegradation* 21(6):861-879, Springer, Netherlands (published online Apr. 2010, published in print Nov. 2010).
Uperlovic-Culf, M., et al., "Cell culture metabolomics: applications and future directions," *Drug Discovery Today* 15(15):610-621, Elsevier, Netherlands (published online Jun. 2010, published in print Aug. 2010).
Vester, J. K., et al., "Improved cultivation and metagenomics as new tools for bioprospecting in cold environments," *Extremophiles* 19(1):17-29, Springer Verlag, Japan (published online Nov. 2014, published in print Jan. 2015).
Goodman, A. L., et al., "Extensive personal human gut microbiota culture collections characterized and manipulated in gnotobiotic mice," *Proc Natl Acad Sci USA* 108(15):6252-6257, National Academy of Science, United States, and 17 pages of Supplemental Information (published online Mar. 2011, published in print Apr. 2011).
Verberkmoes, N. C., et al., "Shotgun metaproteomics of the human distal gut microbiota," *ISME J* 3(2):179-189, Nature Publishing Group, United Kingdom (published online Oct. 2008, published in print Feb. 2009).
Clemente, J. C., et al., "The impact of the gut microbiota on human health: an integrative view," *Cell* 148(6):1258-1270, Cell Press, United States (Mar. 2012).
Jagtap, P., et al., "A two-step database search method improves sensitivity in peptide sequence matches for metaproteomics and proteogenomics studies," *Proteomics* 13(8):1352-1357, Wiley-VCH Verlag, Germany (published online Mar. 2013, published in print Apr. 2013).
Juste, C., et al., "Bacterial protein signals are associated with Crohn's disease," *Gut* 63(10):1566-1577, BMJ Publishing Group, United Kingdom (published online Jan. 2014, published in print Oct. 2014).
Kelly, C. P., "Fecal microbiota transplantation—an old therapy comes of age," *New England Journal of Medicine* 368(5):474-475, Massachusetts Medical Society, United States (Jan. 2013).
Krijgsveld, J., et al., "Metabolic labeling of C. elegans and D. melanogaster for quantitative proteomics," *Nat Biotechnol* 21(8):927-931, Nature Publishing Group, United Kingdom (published online Jul. 2003, published in print Aug. 2003).
Mesuere, B., et al., "Unipept: tryptic peptide-based biodiversity analysis of metaproteome samples," *J Proteome Res* 11(12):5773-5780, American Chemical Society, United States (published online Nov. 2012, published in print Dec. 2012).
Mueller, R. S., et al., "Proteome changes in the initial bacterial colonist during ecological succession in an acid mine drainage biofilm community," *Environmental Microbiology* 13(8):2279-2292, Wiley-Blackwell Publishing Ltd., United Kingdom (published online Apr. 2011, published in print Aug. 2011).
Ong, S-E., et al., "Stable isotope labeling by amino acids in cell culture, SILAC, as a simple and accurate approach to expression proteomics," *Mol Cell Proteomics* 1(5):376-386, Elsevier, Netherlands (May 2002).
Park, S. K., et al., "A quantitative analysis software tool for mass spectrometry-based proteomics," *Nat Methods* 5(4):319-322, Nature Publishing Group, United Kingdom (published online Mar. 2008, published in print Apr. 2008).
Qin, J., et al., "A human gut microbial gene catalogue established by metagenomic sequencing," *Nature* 464(7285):59-65, Nature Publishing Group, United Kingdom (Mar. 2010).
Stahl, M., et al., "L-fucose utilization provides Campylobacter jejuni with a competitive advantage," *Proc Natl Acad Sci USA* 108(17):7194-7199, National Academy of Science, United States (Apr. 2011).
Zhong, S., et al., "A New Rapid In Vitro Assay for Assessing Reactivity of Acyl Glucuronides," *Drug Metabolism and Disposition* 43(11):1711-1717, American Society for Pharmacology and Experimental Therapeutics, United States (published online Aug. 2015, published in print Nov. 2015).
Office Action dated Sep. 17, 2020 in U.S. Appl. No. 16/305,461, inventor Figeys; J.M.D., et al., 371(c) Date: Nov. 29, 2018, 27 pages.
Office Action dated May 14, 2021 in U.S. Appl. No. 16/305,461, inventor Figeys; J.M.D., et al., 371(c) Date: Nov. 29, 2018, 9 pages.
Shen, G.B., et al., "[Application and Development of the SILAC Technique in Proteomics]," *Letters in Biotechnology* 20(2):238-242, Springer Science+Business Media, Germany (2009) (English Translation Appended).
Conrads, Thomas P., et al., "Quantitative Analysis of Bacterial and Mammalian Proteomes Using a Combination of Cysteine Affinity Tags and 15N-Metabolic Labeling," *Anal. Chem.* 73(9):2132-2139, American Chemical Society, United States (2001).

PROTEIN COMPOSITION AND METHODS FOR ANALYSING MICROBIOTA

This application claims priority of U.S. provisional patent application 62/344,247 filed on Jun. 1, 2016.

TECHNICAL FIELD

The present application relates generally to compositions and methods for metaproteomics and more specifically compositions and methods for microbiota protein composition analysis.

BACKGROUND

The human body harbors trillions of microbes which together comprise the human microbiome. Accumulating evidence has associated changes in microbiota composition with many diseases including inflammatory bowel diseases (IBD), obesity, diabetes, cancer, heart disease, urolithiasis, allergies etc. [2]. The microbiome is a highly complex and extremely sensitive system and it has been demonstrated that the microbiome composition is susceptible to alterations due to exposure to various compounds including but not limited to therapeutics, excipients, additives, preservatives, chemicals, stress, exercise, foods and beverages, which can impact both maintenance of health as well as development of disease. In addition to the overall microbiome, organ and region specific microbiomes have been described, in which subsets of these microbes form populations, such as the intestines, skin, vagina, oral cavity, kidney, bladder, eyes, lungs and breasts. Furthermore, it has been shown that the changes induced by many of these environmental, chemical and alimentary compounds have the potential to induce positive changes to these regional microbiomes which improve the composition and diversity of the microbiome, while others induce negative changes consistent with a diseased or unhealthy microbiome. For example, it has been demonstrated that emulsifiers, a ubiquitous component of processed food, causes negative changes in the intestinal microbiome composition indicative of inflammation and disease, while prebiotics have been shown to increase the levels of beneficial microbes, increasing the health of the intestinal microbiome. Exactly how these compositional changes affect overall function, however, remains an outstanding and important question.

One of the largest populations of microbes resides in the gastrointestinal tract and constitutes the intestinal microbiota [1]. The importance of intestinal microbiota for human health was illustrated with the use of fecal microbiota transplantation (FMT) for treating recurrent *Clostridium difficile* infections [3]. Furthermore, it has been shown that the microbiome continues to undergo changes throughout the course of a disease, which was recently demonstrated in IBD in which changes in the intestinal microbiome composition were tightly correlated with disease severity in Crohn's disease. Clearly, the microbiota appears to be involved in the development, progression and resolution of multiple diseases and in some instances, can be modulated to impact disease outcome, making the microbiota of global interest in both scientific and public health communities.

Beyond the human microbiome many additional microbial communities, or microbiomes, have been identified and described. One of the most prominent is the soil microbiome, which is a complex microbial community that can differ by region, climate and cultivation. The composition of the soil microbiome can be assessed to determine biodiversity and the subsequent function of these microbes in the generation and breakdown of nutrients holds wide-ranging implications for agriculture. Biofilms are another well-studied microbiome, which can be of varying complexity, occur in numerous environmental and industrial settings, and can contribute to contamination or toxicity. Understanding the composition and function of the microbes within biofilms is important for understanding biofilm prevention and dissolution. Finally, the microbiome of animals, both in agricultural and lab settings are important to the advancement of food production and research respectively. The microbiome of agricultural animals can be effected by antibiotics as well as feed and these changes have the potential to impact, breeding, animal health and subsequently food production. Additionally, it has recently been recognized that the microbiome of laboratory research animals can have profound effects on their response to therapeutics. A deeper understanding of the microbiome composition and function of these animals could possibly lead to an improved understanding of drug metabolism and the microbiome effect of therapeutic response.

Next-generation sequencing (NGS), such as metagenomics and metatranscriptomics, is well suited for examining the microbiota composition and predicting potential functions, however, it does not provide direct evidence on whether the genes are translated into proteins or not. This information, therefore, does not provide data on changes in the function of the microbiota, which are needed to understand how the alterations in composition impact function and if it is impacted in a physiologically meaningful way. Instead, metaproteomics can provide invaluable information on the functional activities of the microbiome by directly profiling protein expression levels, which are indicative of function [4, 5]. In stark contrast to metagenomics, however, metaproteomics approaches have only been applied to a limited number of studies on the microbiota. This is due, at least in part, to challenges related to both identification and quantification of the microbial peptides/proteins. Peptide/protein identification algorithms have recently been significantly improved by the use of iterative searching of large microbial protein databases [6]. In contrast, accurate methods for peptide/protein quantification are still lacking. Most current metaproteomic approaches are based on label free quantification (LFQ) which suffers from significant variability during the separate sample processing and mass spectrometry runs, making data extremely difficult to compare across experiments or datasets. Stable isotope labeling by amino acids in cell culture (SILAC) and stable isotope labeling of mammals (SILAM) are currently the most widely used approach for quantitative proteomics and provides lower variability [7]. In SILAC/SILAM, proteins in one test or reference sample are metabolically labeled with isotopically heavy amino acids, enabling for quantitative comparison between different samples. However, the application of this approach in bacteria, particularly complex bacterial populations such as the microbiome, has been limited. One of the challenges of applying these metabolic labelling approaches to the microbiota is the inherently high species diversity, which is not present in mammalian cells. Furthermore, the diverse microbiota populations frequently include both aerobic and many anaerobic species, which are extremely difficult to culture in order to achieve sufficient labeling. These complex populations also almost inevitably result in a diverse metabolic capacity to biosynthesize amino acids, which hampers the full incorporation of heavy-labelled amino acids into microbial proteins. Instead, complete metabolic labeling of nitrogen or carbon has only been applied to single bacteria [8], and environmental microbial communities, such as acid mine drainage biofilms [9]. However, its application to characterize the microbiota proteome is lacking.

There is therefore a need for better metaproteomics approach for the analysis of the microbiota.

SUMMARY

A first broad aspect is a fast and cost-effective strategy for metabolic labeling of the whole human microbiota, termed stable isotopically labelled microbiota (SILAMi). It will be understood that by whole human microbiota, it is meant that SILAMi may be used to provide metabolic labeling of any microbiota sample taken from the human microbiota. By samples from the human microbiota, it is meant such samples as, but not limited to samples form the intestinal microbiota, samples from the vaginal microbiota, samples from the oral microbiota, samples from the cutis microbiota, samples from the vaginal microbiota, samples from the bladder microbiota, samples from the kidney microbiota, samples from the lung microbiota, samples from the eye microbiota, samples from the breast microbiota, samples from the penile microbiota, a microbiota mucosal sample, etc. A skilled person will also readily understand that SILAMi can also be applied to a microbiota originating from an animal sample, wherein that animal is, for instance, a mammal, a bird, a reptile, etc.

Applicant has discovered that it is possible to use an isotope-labelling standard for a given microbiota sample having a large microbe population. Prior to the Applicant's discovery, it was believed that the diverse microbiota population could not be labelled simultaneously and that the microbiota would change too rapidly during incorporation of the labelling to achieve a reliable standard that is representative of the original microbiota sampled. However, applicant has discovered that the isotope-labelled standard achieved following the isotope-incorporation process is in fact representative of a significant population of the microbiota of the original sample and the proteins representative thereof. This isotope labelling of the microbiota is entitled SILAMi.

Therefore, SILAMi is a method for achieving the successful labelling of a large microbe population (a microbiota), such as one found in a human or animal subject. Difficulties in obtaining such a standard lie for instance in the fragility and low abundance of some of the microbe species found in the desired microbiota sample, for instance sensitive to changes in environment or exposure to oxygen (e.g. as some of these microbes grow in anaerobic conditions). Moreover, not all of these microbes have the same cell cycle or life cycle, and some take longer to replicate and incorporate the isotope. However, the more time that is taken to grow and incorporate the isotopes in culture, the greater the risk that certain of the species found in the microbiota sample will die off or disproportionately proliferate, not providing a faithful depiction of the microbiota found in the sample as obtained. SILAMi has overcome these prior problems and successfully provides an isotope-labelled standard for a given microbiota from a microbiota sample, where the sample may be taken from, for instance, a human, an animal, soil, plant, water or any other source with a significant population of microbes.

Moreover, Applicant has discovered that using an isotope-labelled standard, such as the one achieved using SILAMi, allows for the study of a large population of microbes in a given microbiota sample. The standard allows for the determination of the functionality and the composition, including changes in the determination of the functionality and composition of the microbiota sample. Furthermore, the standard provides a means of reducing variability when performing a metaproteomic analysis of the microbiota sample. This may be achieved, for instance, by adding a known amount of the standard to the microbiota sample (with a known ratio and measuring the heavy to light ratios for the sample, while comparing the ratios to theoretical known results).

In some examples, the analysis of the microbiota of a subject, such as a human or animal subject, may provide an indication of a disease, illness or other condition afflicting the subject, where these conditions have a measured effect on the microbiota of the subject found at different locations on the subject (e.g. the subject's organs). A comparison between the isotope-labelled standard and the microbiota sample may provide indication, for instance, as to the effectiveness of a treatment, the nature, including diagnosis and therapeutic response to of the disease or illness, the potential for weight gain or loss of the subject, etc.

Another broad aspect is a human microbiota labelled-proteins standard having labelled proteins representative of a metaproteome from a human microbiota as described herein. In some examples, said labelled proteins have at least about 50%, preferable 90%, and more preferably at least about 95% average heavy isotopic enrichment rate.

In a further embodiment there is provided a human intestinal microbiota labelled-proteins standard that may have labelled proteins representative of a metaproteome from an intestinal microbiota. In some embodiments, said labelled proteins may have at least about 90% and preferably at least about 95% average heavy isotopic enrichment rate.

In yet another embodiment the microbiota labelled-proteins standard may be taxon-specific for at least about 90% and preferably at least 95% of the microbes present in the microbiota sample. Preferably the labelled proteins are taxon-specific for 100% of Kingdoms present in the microbiota sample. Preferably the labelled proteins are also taxon-specific for 95% and preferably at least 100% of Phyla present in the microbiota sample. Preferably the labelled proteins are also taxon-specific for at least about 90% and preferably at least 95% of Genera present in the microbiota sample. Preferably the labelled proteins are also taxon-specific for at least about 90% and preferably at least 95% of species present in the microbiota sample.

In yet another embodiment the microbiota labelled-proteins standard may be taxon-specific for at least about 90% and preferably at least 95% of the microbes present in the intestinal microbiota. The labelled proteins may be taxon-specific for 100% of Kingdoms present in the intestinal microbiota. The labelled proteins may also be taxon-specific for 95% and preferably at least 100% of Phyla present in the intestinal microbiota. The labelled proteins may also be taxon-specific for at least about 90% and preferably at least 95% of Genera present in the intestinal microbiota. The labelled proteins may also be taxon-specific for at least about 70% and preferably at least 95% of species present in the intestinal microbiota.

In yet another embodiment the microbiota labelled-proteins standard may be taxon-specific for at least about 90% and preferably at least 95% of the microbes present in the microbiota sample from including but not limited to vaginal, oral, skin, bladder, kidney, lung, eye and breast. The labelled proteins may be taxon-specific for 100% of Kingdoms present in the microbiota. The labelled proteins may also be taxon-specific for 95% and preferably at least 100% of Phyla present in the microbiota. The labelled proteins may be also taxon-specific for at least about 90% and preferably at least 95% of Genera present in the microbiota. The labelled proteins may also be taxon-specific for at least about 90% and preferably at least 95% of the species present in the microbiota.

For an exemplary intestinal microbiota samples, the Domains may be Bacteria, Eukaryota and Archaea, the Phyla are, but not limited to, Bacteroidetes, Proteobacteria, Verrucomicrobia, Fusobacteria, Synergistetes, Thaumarchaeota, Fimicutes, Actinobacteria, Ascomycota, Basidiomycota, Euryarchaeota, Apicomplexa, Arthropoda, Chordata, Nematoda, Streptophyta, the Genera are those listed in table 1, the Species are those listed in table 2.

TABLE 1

An exemplary set of genera that can be found in an exemplary intestinal microbiota sample.

| | | | |
|---|---|---|---|
| Abiotrophia | Edwardsiella | Nitrososphaera | Tyzzerella |
| Acidaminococcus | Eggerthella | Odoribacter | Veillonella |
| Acidovorax | Enterobacter | Oribacterium | Vibrio |
| Acinetobacter | Enterococcus | Oscillibacter | Weissella |
| Actinobacillus | Erwinia | Oxalobacter | Xanthomonas |
| Actinomyces | Erysipelatoclostridium | Paenibacillus | Yokenella |
| Adlercreutzia | Escherichia | Parabacteroides | |
| Aerococcus | Eubacterium | Paraprevotella | |
| Aeromonas | Facklamia | Parasutterella | |
| Akkermansia | Faecalibacterium | Parvimonas | |
| Alcanivorax | Faecalitalea | Pediococcus | |
| Alistipes | Ferrimonas | Peptoclostridium | |
| Alteromonas | Filobasidiella | Peptostreptococcus | |
| Anaerobaculum | Finegoldia | Phascolarctobacterium | |
| Anaerococcus | Flavonifractor | Photobacterium | |
| Anaerofustis | Fusarium | Piscirickettsia | |
| Anaerostipes | Fusobacterium | Plasmodium | |
| Anaerotruncus | Gemella | Porphyromonas | |
| Arcobacter | Gordonibacter | Prevotella | |
| Aspergillus | Granulicatella | Propionibacterium | |
| Atopobium | Haemophilus | Proteus | |
| Bacillus | Hafnia | Providencia | |
| Bacteroides | Hahella | Pseudoflavonifractor | |
| Barnesiella | Helicobacter | Pseudomonas | |
| Bifidobacterium | Holdemanella | Pseudoxanthomonas | |
| Bilophila | Holdemania | Ralstonia | |
| Blautia | Hungatella | Rhodotorula | |
| Burkholderia | Intestinibacter | Roseburia | |
| Butyrivibrio | Klebsiella | Rothia | |
| Campylobacter | Lachnoanaerobaculum | Ruminiclostridium | |
| Candida | Lachnoclostridium | Ruminococcus | |
| Carnobacterium | Lactobacillus | Salmonella | |
| Catenibacterium | Leptotrichia | Selenomonas | |
| Cellvibrio | Leuconostoc | Serratia | |
| Citrobacter | Listeria | Shewanella | |
| Clostridium | Marinomonas | Slackia | |
| Collinsella | Marvinbryantia | Staphylococcus | |
| Coprobacillus | Megamonas | Streptococcus | |
| Coprococcus | Methanobrevibacter | Subdoligranulum | |
| Corynebacterium | Methanosphaera | Succinatimonas | |
| Debaryomyces | Methylobacterium | Sutterella | |
| Desulfitobacterium | Meyerozyma | Synergistes | |
| Desulfovibrio | Mitsuokella | Tannerella | |
| Dialister | Mogibacterium | Terrisporobacter | |
| Dorea | Moraxella | Thermoplasma | |
| Dysgonomonas | Neisseria | Turicibacter | |

TABLE 2

An exemplary set of species that can be found in an exemplary intestinal microbiotasample.

| | |
|---|---|
| Abiotrophia defectiva | Bacteroides intestinalis |
| Acidaminococcus intestini | Bacteroides oleiciplenus |
| Acidovorax avenae | Bacteroides ovatus |
| Acinetobacter junii | Bacteroides pectinophilus |
| Actinobacillus suis | Bacteroides plebeius |
| Actinomyces georgiae | Bacteroides stercoris |
| Actinomyces massiliensis | Bacteroides thetaiotaomicron |
| Actinomyces odontolyticus | Bacteroides uniformis |
| Adlercreutzia equolifaciens | Bacteroides vulgatus |
| Aerococcus viridans | Bacteroides xylanisolvens |
| Aeromonas hydrophila | Barnesiella intestinihominis |
| Aeromonas veronii | Bifidobacterium adolescentis |
| Akkermansia muciniphila | Bifidobacterium angulatum |

TABLE 2-continued

An exemplary set of species that can be found in an exemplary intestinal microbiotasample.

*Alcanivorax dieselolei*
*Alistipes finegoldii*
*Alistipes indistinctus*
*Alistipes putredinis*
*Alistipes shahii*
*Alteromonas macleodii*
*Anaerobaculum hydrogeniformans*
*Anaerococcus hydrogenalis*
*Anaerofustis stercorihominis*
*Anaerostipes caccae*
*Anaerostipes hadrus*
*Anaerotruncus colihominis*
*Arcobacter butzleri*
*Aspergillus fumigatus*
*Atopobium minutum*
*Atopobium parvulum*
*Atopobium rimae*
*Bacillus cereus*
*Bacillus smithii*
*Bacteroides caccae*
*Bacteroides cellulosilyticus*
*Bacteroides clarus*
*Bacteroides coprocola*
*Bacteroides coprophilus*
*Bacteroides dorei*
*Bacteroides eggerthii*
*Bacteroides finegoldii*
*Bacteroides fluxus*
*Bacteroides fragilis*
*Clostridium innocuum*
*Clostridium leptum*
*Clostridium methylpentosum*
*Clostridium perfringens*
*Clostridium saccharolyticum*
*Clostridium scindens*
*Clostridium spiroforme*
*Clostridium symbiosum*
*Collinsella aerofaciens*
*Collinsella intestinalis*
*Collinsella stercoris*
*Collinsella tanakaei*
*Coprococcus catus*
*Coprococcus comes*
*Coprococcus eutactus*
*Corynebacterium ammoniagenes*
*Corynebacterium durum*
*Cryptococcus gattii*
*Debaryomyces hansenii*
*Desulfitobacterium hafniense*
*Desulfovibrio desulfuricans*
*Desulfovibrio piger*
*Dialister invisus*
*Dialister succinatiphilus*
*Dorea formicigenerans*
*Dorea longicatena*
*Dysgonomonas gadei*
*Dysgonomonas mossii*
Edwardsiella tarda
*Eggerthella lenta*
*Enterobacter cancerogenus*
*Enterobacter cloacae*
*Enterococcus faecalis*
*Enterococcus faecium*
*Enterococcus haemoperoxidus*
*Enterococcus saccharolyticus*
*Erwinia amylovora*
*Escherichia coli*
*Eubacterium dolichum*
*Eubacterium hallii*
*Eubacterium rectale*
*Lactobacillus plantarum*
*Lactobacillus reuteri*
*Lactobacillus rhamnosus*
*Lactobacillus ruminis*
*Lactobacillus ultunensis*
*Leptotrichia goodfellowii*
*Leuconostoc mesenteroides*
*Bifidobacterium bifidum*
*Bifidobacterium breve*
*Bifidobacterium catenulatum*
*Bifidobacterium dentium*
*Bifidobacterium gallicum*
*Bifidobacterium longum*
*Bifidobacterium pseudocatenulatum*
*Bilophila wadsworthia*
*Blautia hansenii*
*Blautia hydrogenotrophica*
*Blautia obeum*
*Butyrivibrio crossotus*
*Butyrivibrio fibrisolvens*
*Campylobacter concisus*
*Campylobacter upsaliensis*
*Candida albicans*
*Candidatus Nitrososphaera gargensis*
*Catenibacterium mitsuokai*
*Cellvibrio japonicas*
*Citrobacter freundii*
*Citrobacter youngae*
*Clostridium asparagiforme*
*Clostridium bolteae*
*Clostridium butyricum*
*Clostridium citroniae*
*Clostridium clostridioforme*
*Clostridium hiranonis*
*Clostridium hylemonae*
*Bacteroides intestinalis*
*Eubacterium siraeum*
*Eubacterium ventriosum*
*Facklamia ignava*
*Faecalibacterium prausnitzii*
*Faecalitalea cylindroides*
*Ferrimonas balearica*
*Finegoldia magna*
*Flavonifractor plautii*
*Fusarium graminearum*
*Fusobacterium gonidiaformans*
*Fusobacterium mortiferum*
*Fusobacterium necrophorum*
*Fusobacterium nucleatum*
*Fusobacterium periodonticum*
*Fusobacterium ulcerans*
*Fusobacterium varium*
*Gemella sanguinis*
*Gordonibacter pamelaeae*
*Granulicatella adiacens*
*Hafnia alvei*
*Hahella chejuensis*
*Helicobacter bilis*
*Helicobacter Canadensis*
*Helicobacter cinaedi*
*Helicobacter pullorum*
*Helicobacter pylori*
*Helicobacter winghamensis*
*Holdemanella biformis*
*Holdemania filiformis*
*Hungatella hathewayi*
*Intestinibacter bartlettii*
*Klebsiella pneumoniae*
*Lachnoanaerobaculum saburreum*
*Lactobacillus acidophilus*
*Lactobacillus amylolyticus*
*Lactobacillus antri*
*Lactobacillus brevis*
*Lactobacillus delbrueckii*
*Lactobacillus fermentum*
*Lactobacillus helveticus*
*Lactobacillus iners*
*Prevotella stercorea*
*Prevotella veroralis*
*Propionibacterium acnes*
*Proteus mirabilis*
*Proteus penneri*
*Providencia alcalifaciens*
*Providencia rettgeri*

TABLE 2-continued

An exemplary set of species that can be found in an exemplary intestinal microbiotasample.

| | |
|---|---|
| *Listeria grayi* | *Providencia rustigianii* |
| *Listeria innocua* | *Providencia stuartii* |
| *Marinomonas profundimaris* | *Pseudoflavonifractor capillosus* |
| *Marvinbryantia formatexigens* | *Pseudomonas aeruginosa* |
| *Megamonas funiformis* | *Pseudoxanthomonas spadix* |
| *Megamonas hypermegale* | *Ralstonia pickettii* |
| *Methanobrevibacter smithii* | *Rhodotorula glutinis* |
| *Methanosphaera stadtmanae* | *Roseburia intestinalis* |
| *Methylobacterium nodulans* | *Roseburia inulinivorans* |
| *Meyerozyma guilliermondii* | *Rothia aeria* |
| *Mitsuokella multacida* | *Rothia mucilaginosa* |
| *Mogibacterium timidum* | *Ruminococcus bromii* |
| *Moraxella catarrhalis* | *Ruminococcus champanellensis* |
| *Neisseria bacilliformis* | *Ruminococcus gnavus* |
| *Odoribacter laneus* | *Ruminococcus lactaris* |
| *Oribacterium sinus* | *Ruminococcus torques* |
| *Oxalobacter formigenes* | *Salmonella enterica* |
| *Paenibacillus lactis* | *Selenomonas sputigena* |
| *Parabacteroides distasonis* | *Serratia marcescens* |
| *Parabacteroides johnsonii* | *Shewanella putrefaciens* |
| *Parabacteroides merdae* | *Slackia exigua* |
| *Paraprevotella clara* | *Slackia piriformis* |
| *Paraprevotella xylaniphila* | *Staphylococcus aureus* |
| *Parasutterella excrementihominis* | *Streptococcus equinus* |
| *Parvimonas micra* | *Streptococcus thermophiles* |
| *Pediococcus acidilactici* | *Subdoligranulum variabile* |
| *Peptoclostridium difficile* | *Succinatimonas hippie* |
| *Peptostreptococcus anaerobius* | *Sutterella parvirubra* |
| *Phascolarctobacterium succinatutens* | *Sutterella wadsworthensis* |
| *Photobacterium damselae* | *Terrisporobacter othiniensis* |
| *Piscirickettsia salmonis* | *Thermoplasma volcanium* |
| *Porphyromonas endodontalis* | *Turicibacter sanguinis* |
| *Prevotella copri* | *Tyzzerella nexilis* |
| *Prevotella salivae* | *Veillonella dispar* |
| *Veillonella parvula* | |
| *Weissella paramesenteroides* | |
| *Yokenella regensburgei* | |

In another aspect, the labelled-proteins standard may have isotope(s) labelled proteins and wherein the isotopes(s) can be stable or radioactive isotopes. The isotopes can be selected, for example, from $^{13}C$, $^{14}C$, $^{15}N$, $^{32}S$, $^{35}S$, $^{32}P$ and Deuterium, and combination thereof.

In a further aspect, there is provided a method for obtaining a microbiota labelled-proteins standard, as described above, comprising: obtaining a microbiota sample from an individual; exposing said sample to an isotope enriching growth medium (i.e. an enriched media, such as an isotope enriched media, also defined herein as an isotope enriched medium); and culturing said exposed sample for a period of time sufficient to obtain a predetermined level of enrichment.

In a further aspect, there is provided a method for obtaining a microbiota labelled-proteins standard, as described above, comprising: obtaining a microbiota sample from an individual including but not limited to intestinal, vaginal, oral, skin, bladder, kidney, lung, eye or breast microbiota; exposing said sample to an isotope enriching medium; and culturing said exposed sample for a period of time sufficient to obtain a predetermined level of enrichment.

In another aspect, there is provided a method for measuring an amount of one or more proteins in a microbiota sample comprising obtaining a protein extract from the microbiota sample and spiking the protein extract with the standard, as described above, and obtaining labelled/unlabeled protein ratios of the standard and the one or more bacteria (or, as the case may be, other forms of microbes) in the microbiota sample.

In another aspect, there is also provided a method for measuring an amount of one or more proteins in an intestinal microbiota sample comprising obtaining a protein extract from the microbiota sample and spiking the protein extract with the standard, as described above, and obtaining labelled/unlabeled protein ratios of the standard and the one or more bacteria in the intestinal microbiota sample.

In another aspect, there is also provided a method for measuring an amount of one or more proteins in a microbiota sample comprising obtaining a protein extract from the microbiota sample including but not limited to vaginal, oral, skin, bladder, kidney, lung, eye, or bladder microbiota and spiking the protein extract with the standard, as described above, and obtaining labelled/unlabeled protein ratios of the standard and the one or more bacteria in the microbiota sample.

The method for measuring an amount of one or more proteins in an microbiota sample may further comprise obtaining a label free quantification (LFQ) of the microbiota sample. The SILAMi and LFQ method can be combined to improve the accuracy of protein measurement in a sample. The method may also involve performing gas chromatography/mass spectrometry. In some embodiments, the method may involve performing mass spectrometry.

In some embodiments, the method for measuring an amount of one or more proteins in an intestinal microbiota sample may further comprise obtaining a label free quantification (LFQ) of the intestinal microbiota sample. The SILAMi and LFQ method can be combined to improve the accuracy of protein measurement in a sample.

The method for measuring an amount of one or more proteins in a microbiota sample including but not limited to vaginal, oral, skin, bladder, kidney, lung, eye, or bladder microbiota may further comprise obtaining a label free quantification (LFQ) of the microbiota sample. The SILAMi and LFQ method can be combined to improve the accuracy of protein measurement in a sample In yet another embodiment there is provided a method for diagnosing a disease such as, but not limited to, an intestinal disease (IBD for example) comprising measuring an amount of one or more proteins in a microbiota sample (wherein the measuring is performed using the standard such as described with respect to the method for measuring an amount of one or more proteins in a microbiota sample as described herein) from a patient and wherein deviation from normal is indicative of disease. In an aspect of this method the measuring is performed at one or more time point and is compared to control samples optimally obtained at a predetermined time in the life of an individual or from an individual in a predetermined state of health.

A method for treating a patient with a disease is also provided that involves assessing said patient's microbiota as described above to diagnose the disease and treating the patient according to the diagnostic.

In yet another aspect, there is provided a method for determining treatment response in a patient with a disease comprising measuring one or more proteins in a microbiota sample from a patient and wherein derivation away from diseased and/or toward normal is indicative of favorable treatment response. In an aspect of this method the measuring is performed at a one or more time point and is compared to control samples optimally obtained at a predetermined time in the life of an individual or from an individual in a predetermined state of health or disease.

In yet another aspect, there is provided a method for determining remission in a patient with a disease comprising measuring one or more proteins in a microbiota sample from a patient and wherein normal levels are indicative of the absence of a previously present disease. In an aspect of this method the measuring is performed at a one or more time point and is compared to control and/or disease samples optimally obtained at a predetermined time in the life of an individual or from an individual in a predetermined state of health or disease.

In another aspect there is provided a method for screening xenobiotics effect on a human microbiota comprising exposing the microbiota to one or more xenobiotics and measuring an amount of one or more protein as described above.

In another aspect, there is provided a method for screening xenobiotics effect on a human microbiota, including but not limited to intestinal, vaginal, oral, skin, bladder, kidney, lung, eye and breast microbiome, comprising exposing the microbiota to one or more xenobiotics and measuring an amount of one or more protein as described above.

In another aspect, there is provided a method for screening xenobiotics effect on an intestinal human microbiota comprising exposing the microbiota to one or more xenobiotics, including but not limited to chemicals, toxins, environmental toxins, and poisons and measuring an amount of one or more protein as described above.

From the screening of xenobiotics effect a profile may be generated based on proteins measurements. The profile can be integrated into a method of diagnostic or prognostic.

In a further aspect, there is provided a method for screening the effect of therapeutics on a human microbiota, including but not limited to immunotherapies, antibiotics, checkpoint inhibitors, chemotherapies, antidepressants, antiepileptic, antiemetic, analgesics, antivirals, sedatives, antidiabetic, antipsychotics, and anticoagulants, comprising exposing the microbiota to one or more drugs and measuring the amount of one or more proteins as described above.

In a further aspect, there is provided a method for screening the effect of therapeutics on a human microbiota, using the RapidAIM and/or SILAMi technique disclosed herein, including but not limited to therapies or antibodies targeted to, PD-1/PDCD1/CD279; PD-L1/CD274; PD-L2/PDCD1LG2; CTLA-4/CD152; CD80/B7/B7-1; CD86; TIM-3/HAVCR2; Galectin-9/GAL9/LGALS9; TIGIT; CD155/PVR; LAG3; VISTA/C10orf54; B7-H3/CD276; B7-H4/VTCN1; BTLA/CD272; HVEM/TR2/TNFRSF14; A2AR; CD28; CD80/B7/B7-1; CD86; ICOS/CD278; CD275/ICOSLG/B7RP1; CD40L/CD154; CD40; CD137/4-1BB; CD137L; CD27; CD70/CD27L; OX40/CD134/TNFRSF4; OX40L/TNFSF4; GITR; GITRL; SIRPα; CD47 comprising exposing the microbiota to one or more drugs and measuring the amount of one or more proteins as described above.

In a further aspect, there is provided a method for screening the effect of foods on a human microbiota comprising exposing the microbiota to one or more foods and measuring the amount of one or more proteins as described above.

In a further aspect, there is provided a method for screening the effect of food ingredients on a human microbiota, including but not limited to food additives, amino acids, flavorings, dyes, emulsifiers, sweetners, hydrocolloids and preservatives, comprising exposing the microbiota to one or more ingredients and measuring the amount of one or more proteins as described above.

In a further aspect, there is provided a method for screening the effect of beverages on a human microbiota, including but not limited to soda, sports beverages, infant formula, milk, alcohol, juice, drinkable yogurt, and fermented teas, comprising exposing the microbiota to one or more beverages and measuring the amount of one or more proteins as described above.

In another aspect, there is provided a method for screening the effect of packaging components on a human microbiota, including but not limited to coatings and plastics, comprising exposing the microbiota to one or more packaging component and measuring the amount of one or more proteins as described above.

In another aspect, there is provided a method for screening the effect of cosmetics and cosmetic components including but not limited to excipients, natural and synthetic pigments, thickeners, and emulsifiers, on a human microbiota, comprising exposing the microbiota to one or more cosmetics or cosmetic components and measuring the amount of one or more proteins as described above.

In another aspect, there is provided a method for screening the effect of consumer products including but not limited to infant products, household cleaners, lotions, shampoos and perfumes on a human microbiota, comprising exposing the microbiota to one or more consumer products and measuring the amount of one or more proteins as described above.

In another aspect, there is provided a method for screening the effect of consumer health products including but not limited to supplements, vitamins, amino acids, and plant extracts on a human microbiota, comprising exposing the microbiota to one or more consumer products and measuring the amount of one or more proteins as described above In another aspect, there is provided a fast and cost-effective method for metabolic labeling of a soil microbiota. The method for obtaining a soil microbiota labelled-proteins standard, as described above, involves obtaining a soil microbiota sample; exposing said sample to an isotope enriching medium; and culturing said exposed sample for a period of time sufficient to obtain a pre-determined level of enrichment.

Another aspect is a method for measuring an amount of one or more proteins in a soil microbiota sample comprising obtaining a protein extract from the microbiota sample and spiking the protein extract with the standard, as described above, and obtaining labelled/unlabeled protein ratios of the standard and the one or more bacteria in the microbiota sample.

In another aspect, there is provided a method for screening xenobiotics effect on a soil microbiota, involving exposing the microbiota to one or more xenobiotics including but not limited to pesticides, toxins, amino acids, and nitrates and then measuring an amount of one or more proteins.

In another aspect, there is provided a fast and cost-effective method for metabolic labeling of an animal microbiota, wherein the animal microbiota may originate from a microbiota sample from an animal, such as a cow, pig, chicken, llama, sheep, goat, rabbit, mouse, rat, etc.

In a further aspect, there is provided a method for obtaining an animal microbiota labelled-proteins standard, as described above, involving obtaining an animal microbiota sample such as a cow, pig, chicken, llama, sheep, goat, rabbit, mouse, rat, etc; exposing said sample to an isotope enriching medium; and culturing said exposed sample for a period of time sufficient to obtain a pre-determined level of enrichment.

In yet another aspect there is provided a method for diagnosing a disease including measuring an amount of one or more proteins in a microbiota sample from an animal, including but not limited to cows, pigs, chickens, llamas, sheep, goats, rabbits, mice and rats and wherein deviation from normal is indicative of disease. In an aspect of this method the measuring is performed at a one or more time point and is compared to control samples optionally obtained at a predetermined time in the life of an animal or from an animal in a pre-determined state of health.

In another aspect there is provided a method for screening xenobiotics effect on an animal microbiota, including but not limited to cows, pigs, chickens, llamas, sheep, goats, rabbits, mice and rats; comprising exposing the microbiota to one or more xenobiotics, including but not limited to feed, amino acids, supplements, pesticides, and toxins, and measuring an amount of one or more proteins.

In one aspect, there is provided a fast and cost-effective method for metabolic labeling of a biofilm microbiota. The method for screening xenobiotics effect on a biofilm microbiota; includes exposing the microbiota to one or more xenobiotics, including but not limited to chemicals, pesticides, toxins, and soaps, and measuring an amount of one or more proteins.

In another aspect, there is provided a fast and cost-effective strategy for metabolic labeling of a microbiota from an industrial manufacturing facility.

Another broad aspect is a method of labelling a microbiota sample that includes providing a microbiota sample that was obtained from a given source. The method involves exposing the microbiota sample to an enriched medium, and culturing the microbiota sample to obtain a microbiota sample with a labeled proteome. In some embodiments, the labelled microbiota sample may be taxon specific for taxa present in the first microbiota sample when initially obtained from the given source.

In some embodiments, the enriched medium may be an isotope enriched medium, wherein the proteome of the microbiota sample may be isotope-labelled. However, the label enriched medium may provide for labelling other than isotopes.

Another broad aspect is a microbiota labelled-proteins standard obtained by performing the method of obtaining a labelled microbiota sample as defined herein, wherein the microbiota labelled-proteins standard has labelled proteins representative of a proteome from a selected microbiota.

Another broad aspect is a method for labelling protein of a microbiota sample comprising providing a first microbiota sample that was obtained from a given source; exposing the first microbiota sample to an enriched medium; and culturing the exposed first microbiota sample in the enriched medium to obtain an labelled microbiota sample, wherein the labelled metaproteome of the labelled microbiota sample is taxon specific for taxa present in the first microbiota sample when initially obtained from the given source. In some embodiments, the method may further comprise characterizing said labelled microbiota sample by performing a metaproteomic analysis of said labelled microbiota sample. In some embodiments, said labelled microbiota sample may be taxon specific for a predetermined proportion of microbe populations present in the first microbiota sample when initially obtained from the given source. In some embodiments, the enriched medium may be an isotope enriched medium.

In some embodiments, the labelled microbiota sample is taxon specific for a predetermined proportion of microbe populations present in the first microbiota sample when initially obtained from the given source. By pre-determined proportion it is meant that some taxa of microbes are specifically sought to be labelled in the labelling of the labelled sample. For instance, a user may be searching for specific bacterial species that are associated with a given disease (e.g. atopobium parvulum in the case of certain intestinal disease). In this example, the pre-determined proportion would be or would include the bacterial species that are known for that disease. Moreover, certain microbial populations may be known to react positively or negatively when a patient is given a specific compound (e.g. a drug) or when a patient is responding to a given diagnostic treatment. In these examples, the pre-determined populations may be or may include those reactive microbial populations or taxa.

In some embodiments, the method may involve characterizing the labelled microbiota sample by performing a metaproteomic analysis of the -labelled microbiota sample. The culturing of the exposed first microbiota sample may be for a period to obtain an average level of enrichment of the labelled proteins representative of the metaproteome of at least 70% and to be taxon specific for a predetermined proportion of microbe populations present in the first microbiota sample when initially obtained from the given source.

The culturing of the exposed first microbiota sample may be for a period to obtain an average level of enrichment of the labelled proteins representative of the metaproteome of at least 90% and to be taxon specific for a predetermined proportion of microbe populations present in the first microbiota sample when initially obtained from the given source. The culturing of the exposed first microbiota sample may be for a period to obtain an average level of enrichment of the labelled proteins representative of the metaproteome of at least 95% and to be taxon specific for a predetermined proportion of microbe populations present in the first microbiota sample when initially obtained from the given source. The culturing the exposed first microbiota sample may be for a period to obtain a predetermined average level of enrichment of the labelled proteins representative of the metaproteome of the exposed first microbiota sample and to be taxon specific for at least 50% of the microbe populations present in the first microbiota sample when initially obtained from the given source. The culturing the exposed first microbiota sample may be for a period to obtain a predetermined average level of enrichment of the labelled proteins representative of the metaproteome of the exposed first microbiota sample and to be taxon specific for at least 90% of the microbe populations present in the first microbiota sample when initially obtained from the given source. The culturing the exposed first microbiota sample may be for a period to obtain a predetermined average level of enrichment of the labelled proteins representative of the metaproteome of the exposed first microbiota sample and to be taxon specific for 90% of Phyla present in the first microbiota sample when initially obtained from the given source. The culturing the exposed first microbiota sample may be for a period to obtain a predetermined average level of enrichment of the labelled proteins representative of the metaproteome of the exposed first microbiota sample and to be taxon specific for at least about 90% of Genera present in the first microbiota sample when initially obtained from the given source. The culturing the exposed first microbiota sample may be for a period to obtain a predetermined average level of enrichment of the labelled proteins representative of the metaproteome of the exposed first microbiota sample and to be taxon specific for at least about 90% of species present in the first microbiota sample when initially obtained from the given source.

In some embodiments, an isotope enriched medium to which the first microbiota sample is exposed may contain an isotope selected from 13C, 14C, 15N, 32S, 35S, 32P and Deuterium, and combination thereof. The isotope enriched medium to which the microbiota sample is exposed may contain as an isotope 15N.

In some embodiments, the first microbiota sample that is provided may be obtained from a human subject. In other embodiments, the first microbiota sample that is provided may be obtained from an animal subject.

the providing a first microbiota sample may be providing a type of microbiota sample, wherein the microbiota sample type may be an intestinal microbiota sample, a cutis microbiota sample, a vaginal microbiota sample, an oral microbiota sample, a lung microbiota sample, a mucosal microbiota sample, a bladder microbiota sample, a kidney microbiota sample, an eye microbiota sample, a penile microbiota sample, or a breast microbiota sample.

Another broad aspect may be a method of performing a compositional analysis of a second microbiota sample that involves using a labelled microbiota sample, obtained by performing a method such a sample as described herein, as a labelled standard to perform compositional analysis of a second microbiota sample, wherein the compositional analysis is enhanced as a result of the employment of the labelled-standard.

The compositional analysis may be performed on a second microbiota sample having a same microbiota sample type as that of the first microbiota sample. The method may include, prior to the employing the labelled-standard to perform compositional analysis of a second microbiota sample, providing the second microbiota sample that was obtained from the same source as the microbiota sample used to obtain the labelled standard. The using a labelled microbiota sample as a labelled standard to perform compositional analysis of a second microbiota sample may include performing metaproteomic analysis, and the metaproteomic analysis may be for measuring an amount of one or more protein in the second microbiota sample. The metaproteomic analysis may include obtaining a protein extract from the second microbiota sample, spiking the protein extract with the labelled standard; and obtaining labelled/unlabelled protein ratios of the labelled standard and the one or more protein in the second microbiota sample. The metaproteomic analysis may also involve obtaining a label free quantification (LFQ) of the second microbiota sample. The using a labelled microbiota sample as a labelled standard to perform compositional analysis of a second microbiota sample may involve performing metagenomic analysis. In some embodiments, the metagenomic analysis may involve 16S-based sequencing. The metagenomic analysis may involve shotgun sequencing.

The compositional analysis may be performed to achieve disease diagnosis in a target subject, assessing treatment response in a target subject, assessing remission in a subject receiving treatment, screening for xenobiotic effects on a microbiome of a target subject, screening for effects of a compound on a microbiome of a target subject, wherein the compound is one of a food, a drug, a chemical, a therapeutic agent, a toxin, a poison, a beverage, a food additive, a cosmetic, a cosmetic ingredient, packaging material, a pesticide, a herbicide, a consumer product, and/or screening a microbiome to identify the responsiveness of a subject to a therapy or treatment.

The compositional analysis may be performed to achieve the screening for xenobiotic effects on a microbiome of a target subject, and the second microbiota sample may be obtained from the target subject, and the compositional analysis may be performed subsequent to the target subject being exposed to one or more xenobiotics. The compositional analysis may be performed to achieve screening for effects of a compound on a microbiome of a target subject, wherein the second microbiota sample may be obtained from the target subject, and the compositional analysis may be performed subsequent to the target subject being exposed to one or more compounds. A profile may be generated based on the compositional analysis. The profile may be integrated into a method of diagnosis or prognosis. The compositional analysis may be performed to achieve the disease diagnosis in a target subject, wherein the using a labelled microbiota sample as a labelled standard to perform compositional analysis may also include measuring an amount of the one or more protein in the second microbiota sample and wherein deviation from normal is indicative of the disease. The metaproteomic analysis may be performed at one or more time points using a time-point microbiota sample taken at the one or more time points, and, following a metaproteomic analysis performed on the time-point microbiota sample, a measured one or more proteins from the time-point microbiota sample may be compared to a control sample. The control sample may be a standard control sample taken from a subject in a predetermined state of health, and/or a control sample obtained at a predetermined time in the life of the target subject. Another broad aspect is a method for treating a patient with a disease comprising assessing the patient's microbiota to diagnose the disease and treat the patient in accordance with the diagnostic.

Another broad aspect is a method of high throughput screening of multiple microbiota samples for metaproteomic analysis of the samples. The method entails culturing multiple microbiota samples wherein each sample of the multiple microbiota samples is cultured in a well of a multi-well receptacle. The method involves washing the cells of the multiple microbiota culture samples, re-suspending in lysis buffer with a protease inhibitor the microbiota culture samples, lysing the cells of the multiple microbiota culture samples, diluting the multiple microbiota culture samples, and digesting the proteins contained in the microbiota culture samples. The method adds performing simultaneous metaproteome identification and quantification of the multiple microbiota samples by using a microbial gene catalog of a given subject type and an iterative database search strategy.

In some embodiments, the microbial gene catalog of a given subject type is a microbial gene catalog of a human. In some embodiments, the microbial gene catalog of a given subject type may be a microbial gene catalog of an animal.

In some embodiments, prior to digesting the proteins contained in the microbiota culture samples, the method may involve spiking the microbiota culture samples with an isotope labelled standard corresponding to a given microbiota sample. In some embodiments, prior to the digesting, the method may involve reducing and alkylating of cysteines in the proteins contained in the microbiota culture samples. The spiking may involve adding sufficient isotope labelled-standard to reach a 1:1 protein mass ratio with the protein contained in the microbiota culture samples.

In some embodiments, the multi-well receptacle is a multi-well plate.

In some embodiments, the method may involve assessing the results of the metaproteome identification and quantification of the multiple microbiota samples to perform disease diagnosis in a target subject, assessing treatment response in a target subject, assessing remission in a subject receiving treatment, screening for xenobiotic effects on a microbiome of a target subject, screening for effects of a compound on a microbiome of a target subject, wherein the compound is one of a food, a drug, a chemical, a therapeutic agent, a toxin, a poison, a beverage, a food additive, a cosmetic, a cosmetic ingredient, packaging material, a pesticide, a herbicide, a consumer product, and/or screening a microbiome to identify the responsiveness of a subject to a therapy or treatment.

Another broad aspect is a method of high throughput screening of multiple microbiota samples for meta-omic analysis of the samples includes providing a plurality of microbiota samples in culture. The method also involves performing a pre-screening using a meta-omic technique to identify changes in microbiomes of the microbiota samples, selecting the microbiomes exhibiting predetermined changes, and analyzing the selected microbiomes to characterize the changes. The provided microbiota samples may be cultured in micro-well receptacles. The provided microbiota samples may be cultured in micro-well plates.

In some embodiments, the analyzing may involve using a microbial gene catalog of a given subject type and an iterative database search strategy. The analyzing may involve performing a metaproteomic analysis combined with a metagenomic analysis. The microbial gene catalog of a given subject type may be a microbial gene catalog of a human. The microbial gene catalog of a given subject type may be a microbial gene catalog of an animal.

In some embodiments, the method may involve, after the providing, spiking the plurality microbiota culture samples with an isotope labelled standard corresponding to a given microbiota sample. The spiking may involve adding sufficient isotope labelled-standard to reach a 1:1 protein mass ratio with the protein contained in the plurality of microbiota culture samples. The performing a pre-screening using a meta-omic technique may involve performing metaproteomics.

The method may involve assessing the results of the analysis of the selected microbiomes to perform disease diagnosis in a target subject; assessing treatment response in a target subject; assessing remission in a subject receiving treatment; screening for xenobiotic effects on a microbiome of a target subject; screening for effects of a compound on a microbiome of a target subject, wherein the compound is one of a food, a drug, a chemical, a therapeutic agent, a toxin, a poison, a beverage, a food additive, a cosmetic, a cosmetic ingredient, packaging material, a pesticide, a herbicide, a consumer product; and/or screening a microbiome to identify the responsiveness of a subject to a therapy or treatment.

Another aspect is a method for isotope-labelling protein of a microbiota sample comprising:

providing a first microbiota sample that was obtained from a given source;

exposing said first microbiota sample to an isotope enriched medium; and culturing said exposed first microbiota sample in said isotope enriched medium to obtain an isotope-labelled microbiota sample, wherein the isotope labelled metaproteome of said isotope-labelled microbiota sample is taxon specific for taxa present in said first microbiota sample when initially obtained from said given source.

BRIEF DESCRIPTION OF THE DRAWINGS

The invention will be better understood by way of the following detailed description of embodiments of the invention with reference to the appended drawings, in which:

FIG. 10 illustrates exemplary results from a RapidAIM assay for samples treated with a high (4-BBH), medium (3-BBM) or low (2-BBL) dose of berberine compared to a sample that is normal control (1-CN). The taxonomic composition at the species level were quantified in each of the cultured microbiome sample on the MetaLab bioinformatics platform.

DETAILED DESCRIPTION

SILAMi is a labelling technique that yields an isotope-labelled standard for a given microbiota sample. The original microbiota sample may have a large diversity of microbes. The microbe populations contained in the sample may range from prokaryotes (bacteria and archaea) to eukaryotes, where the eukaryotes may include fungi, protists.

In SILAMi, microbiota samples are inoculated into $^{15}$N-labeled bacterial growth media, cultured under anaerobic conditions and passaged every 24 hours. Once the $^{15}$N isotope is incorporated, the labelled microbiota can be used as an internal standard for the study of unlabelled samples. In the examples provided herein, a fresh intestinal microbiota sample was used. However, the skilled person will readily understand that other microbiota samples may be obtained and used in SILAMi without departing from the present teachings.

In the present application, by "compositional analysis" it is meant an analysis technique to determine the composition of a microbiota sample. Such analysis may involve, for example, metaproteomic analysis, metagenomic analysis or any other analytical technique employed to determine the composition (may it be the protein composition, the microbe composition), or a combination thereof, of the microbiota sample.

Moreover, by "microbe populations" it is meant the different taxa present in a microbiota (this includes, for example, the Domain, Kingdom, Phyla, Class, Order, Family Genera, Species found in the sample). In some examples, the microbe populations as herein defined may relate to the microdiversity of a microbiota sample, or to the diverse taxa found in the microbiota sample.

Figure 1A:
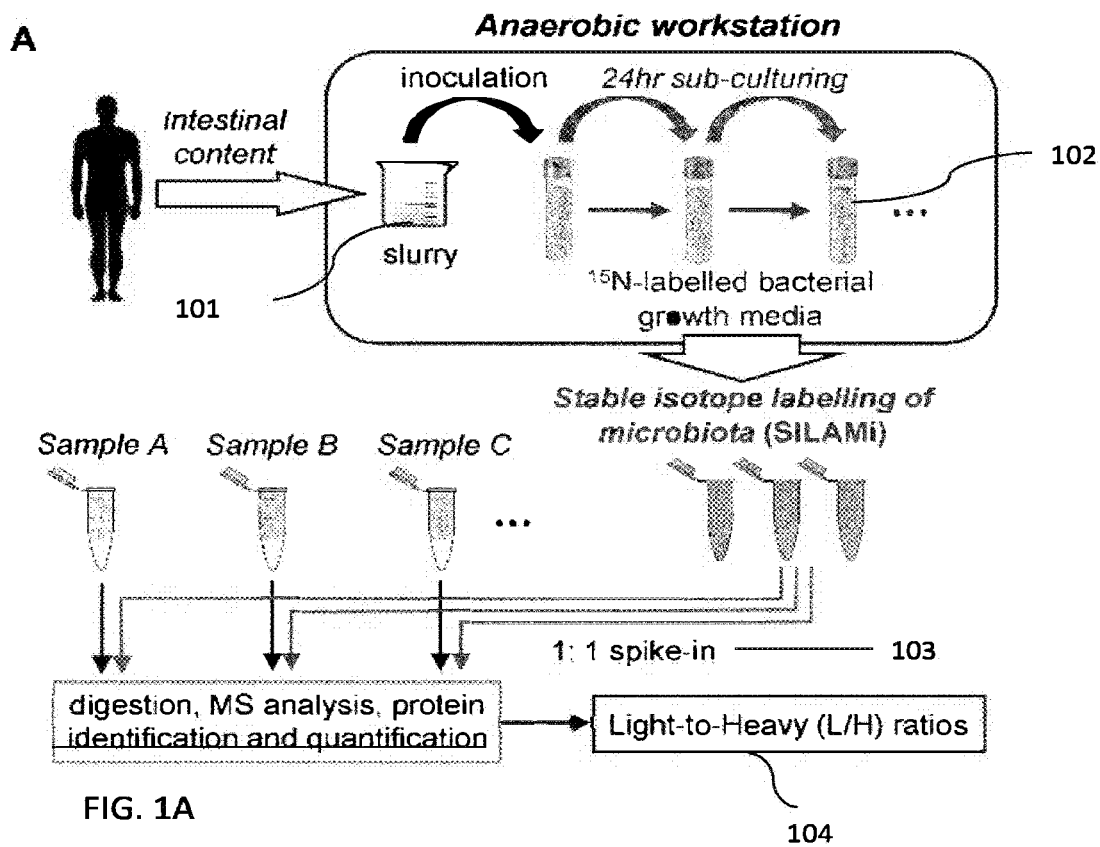
FIG. 1 is a schematic diagram of the exemplary labelling method comprising isotopic $^{15}N$ metabolic labeling of human microbiota for quantitative metaproteomics. (A) Brief workflow of the stable isotope labeling of microbiota (SILAMi), and the SILAMi-based quantitative metaproteomic approaches, which can be applied to any human microbiota sample. (B) $^{15}N$ isotopic enrichment of identified intestinal microbial peptides. Mucosal-luminal interface aspirate samples, or stool samples yielding slurries from five different individuals were labelled separately with three technical replicates. The average $^{15}N$ enrichment rates of all the identified peptides for each individual's microbiota were shown. It will be understood that even though a Mucosal-luminal interface aspirate samples or a stool sample (slurry) were used as a microbiota sample, any intestinal microbiota sample may be used to perform the following method. Moreover, a skilled person will understand that any microbiota sample used from a human or animal may be used when performing the following method.

By "microbiota sample" it is meant a sample that contains a microbiota from a particular source. Even though the experiments described herein focus upon microbiota samples originating from a human (e.g. an intestine of a human as shown in FIG. 1A and following), it will be understood that these are but examples of the fact that an isotope-labelled standard may be achieved for such a diverse population as that found in a human subject. Therefore, it will be appreciated by a skilled person in the art that other microbiota samples may similarly be obtained and cultured to reach an isotope-labelled standard by employing the SILAMi technique as described herein. For example, it will be readily understood that such microbiota samples may originate from animals, soil or water, and may even involve certain plants with a diverse microbiota population residing therein or thereon.

By "isotopically metabolic labelling" it is meant the technique of incorporating isotopes into a given microbiota population as described herein.

Experiment 1: Effectiveness of the SILAMi Technique to Label a Diverse Microbe Population:

In an experiment to demonstrate the efficacy of the SILAMi microbiome labeling technique in a diverse mixed microbe populations, it was first examined whether intestinal metaproteomes could be efficiently labeled with $^{15}$N. The intestinal metaproteome was selected for this experiment due to its diverse microbiome—indicative that other diverse microbiomes may similarly be labelled to provide isotope-labelled standards and importance in intestinal disease.

Experiment Protocol:

Five intestinal microbiome samples were aspirated from colons. In some examples, as shown in FIG. 1A, the samples may be obtained from stool 101 of subjects. The microbiota samples were transported to an anaerobic workstation (37° C., 10% H2, 10% CO2, and 80% N2) for processing and culturing. The samples were individually cultured in 15N-labeled growth media for 5 days 102 (passages) and kept during this time in anaerobic conditions. An optimized enriched media that is used may be modified dependent upon the microbiota sample used. In some embodiments, a skilled person will understand the enriched media used may be adapted to be suitable for the particular microbiota sample. For instance, in the case of the present intestinal microbiota samples, a 15N bacteria growth medium was supplemented with 0.1% w/v sodium thioglycolate and a 0.5 g/L bile salts mixture to accommodate intestinal bacteria. It will be understood that other adjustments may be made in order to provide a suitable growth medium that may be used in combination with other and/or additional labelled isotopes for the microbiome found in the sample. Moreover, it will be understood that the growth medium may include other isotopes that are to be incorporated into the microbiota. Even though 15N was used for the present intestinal microbiota sample, other isotopes may be used depending upon the nature of the microbiota present within the sample, the point of origination of the sample itself, and the desired labelling (e.g. a sulfur isotope may be used if only cysteine is to be labelled).

Figure 1B:
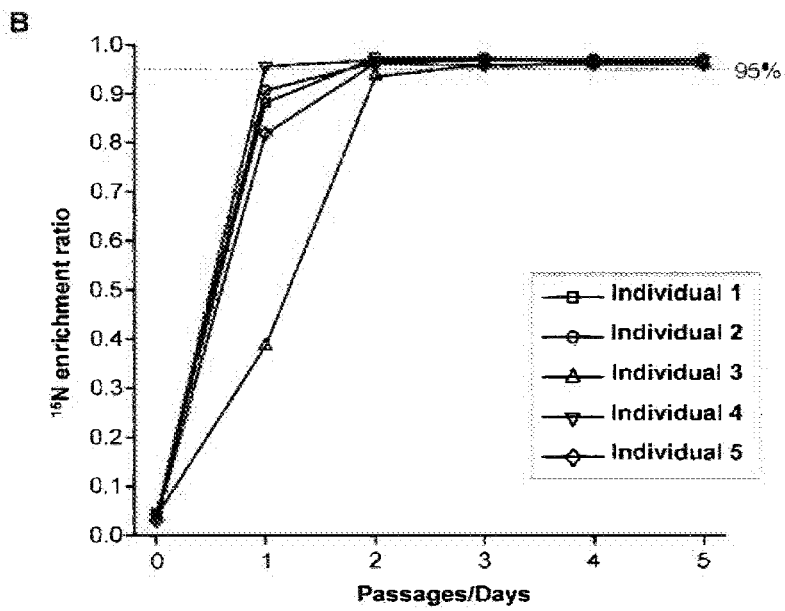

Results:

After each passage 102, as shown in FIG. 1A, the microbiota sample was analyzed by mass spectrometry, as is known in the art, to determine the 15N enrichment level of the microbiota sample. These results are shown in FIG. 1B. As illustrated in FIG. 1B, for the five individuals tested, the 15N enrichment rate of the samples was approximately 95% after two passages. This illustrates that it is possible to achieve a high isotope enrichment rate for a microbiota sample with a diverse microbe population (e.g. a microbiota sample originating from the intestine). A skilled person will appreciate that even though an intestinal microbiota sample was used in the present experiment to achieve this high enrichment rate, such isotope enrichment may be achieved by using other microbiota populations with a diverse microbe population, other than the one found in the intestine of a human subject (e.g. lung microbiota, cutis microbiota). Moreover, based upon these results, such microbiota samples may also be obtained from animal subjects, wherein animal subjects similarly have diverse microbial populations.

Moreover, for certain microbiota samples exposed to air (and oxygen), it may not be necessary to maintain anaerobic conditions.

Furthermore, a skilled person will also understand that by using other isotope enriched growth media, where the isotope is one other that 15N, it is appreciated that labelling a microbiota sample with other isotopes can be performed while still yielding a high enrichment rate, based upon these results, as presented in FIG. 1B.

The metaproteomes were analyzed by mass spectrometry. It will be readily understood that gas chromatography-mass spectrometry may also be used. It will be readily understood that the intestinal microbiota sample was selected because of its diversity of microbiota to demonstrate SILAMi's ability to provide a standard for such a complex microbiota population. However, it will be apparent that any other microbiota population with a diverse microbiota may be similarly used without departing from the present teachings (e.g. mucosal, lung, cutis, etc.).

Figure 4:
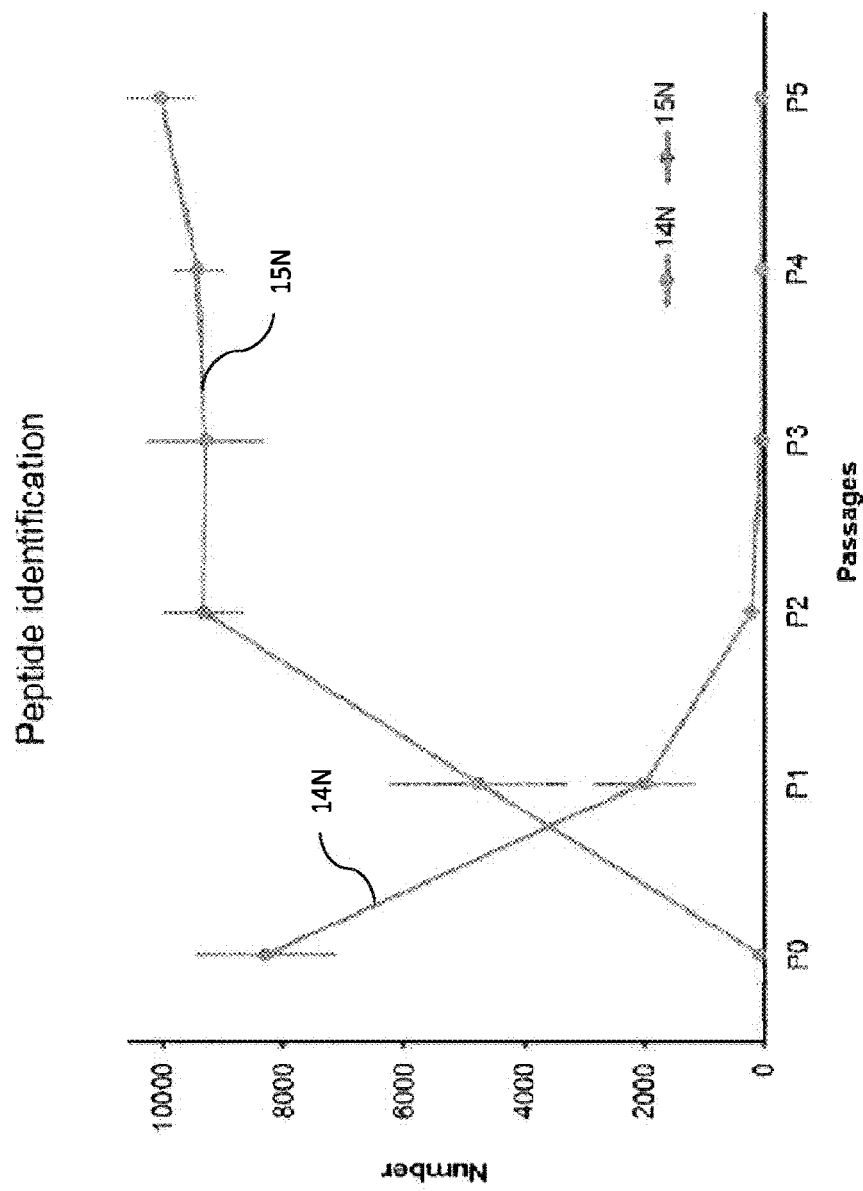
FIG. 4 is a graph illustrating $^{14}$N and $^{15}$N peptide identification for each passage of the five human intestinal microbiota samples during metabolic labeling. The mean and standard error of the identified unique peptide sequences are shown.

Moreover, the number of peptides identified with complete $^{15}$N labeling increased (up to 11,800 peptides/sample after three days labeling), while the unlabeled peptides were minimally identified (less than 100 peptides/sample; FIG. 4). Percent atomic enrichment calculation using Census [10] also showed that all five microbiota tested reached an average $^{15}$N enrichment of >95%, which is more than sufficient for $^{15}$N-based quantitative proteomics, within three passages/days (FIG. 1B). However, even though over 95% enrichment rate is explained herein as being sufficient for quantitative proteomics as illustrated in the example of FIG. 1B, showing a very high and optimal enrichment rate, it will be understood by a person skilled in the art that the enrichment rate for quantitative proteomics may be anywhere over 50% and still provide acceptable results. In some examples, an enrichment rate of over 90%, as shown for the majority of subjects after 1 passage in FIG. 1B, is sufficient for quantitative proteomics or any other compositional analysis. These data demonstrate that this technique is capable of efficiently labeling a complex and metabolically diverse population of microbes.

Figure 5:
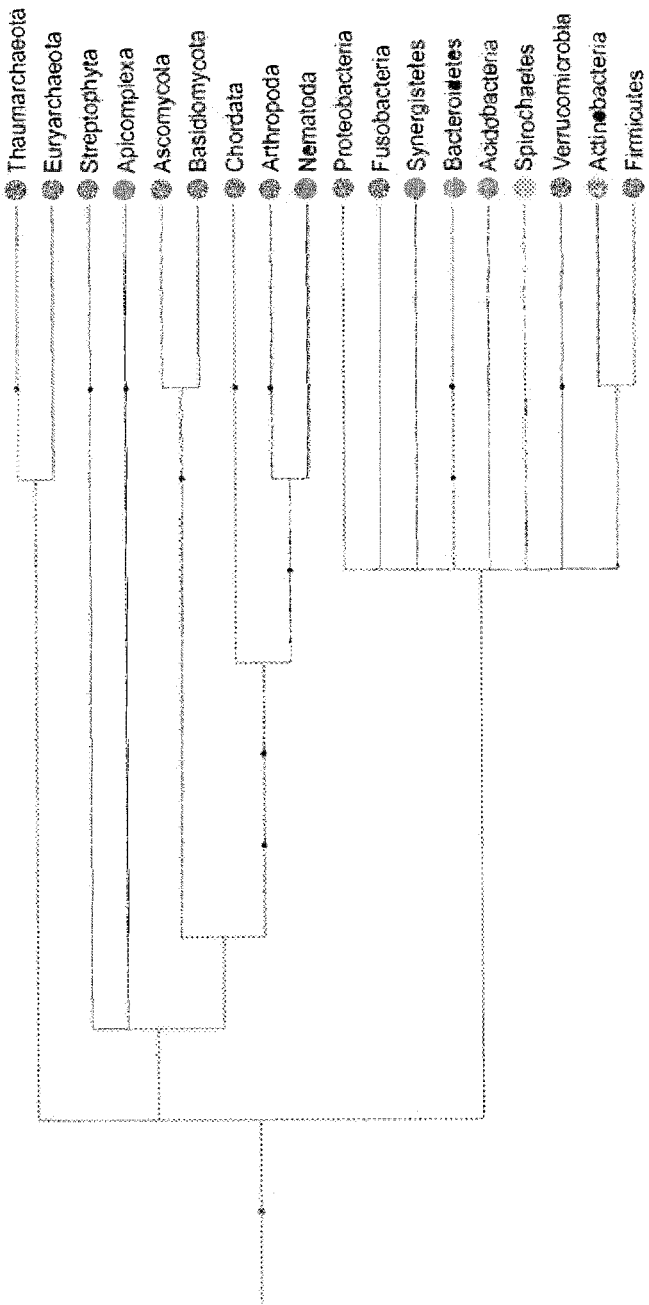
FIG. 5 illustrates microbiota composition at the initial inoculum (Passage 0) and SILAMi at phylum and genus levels. Taxonomic analysis was performed using metaproteomics. For metaproteomic analysis, phyla (A) and genera (B) were considered present if they had ≥2 detected unique peptide sequences. Orange indicates the presence of the taxa in only Passage 0, while purple indicates the taxa are present at both Passage 0 and in SILAMi.
Figure 5:
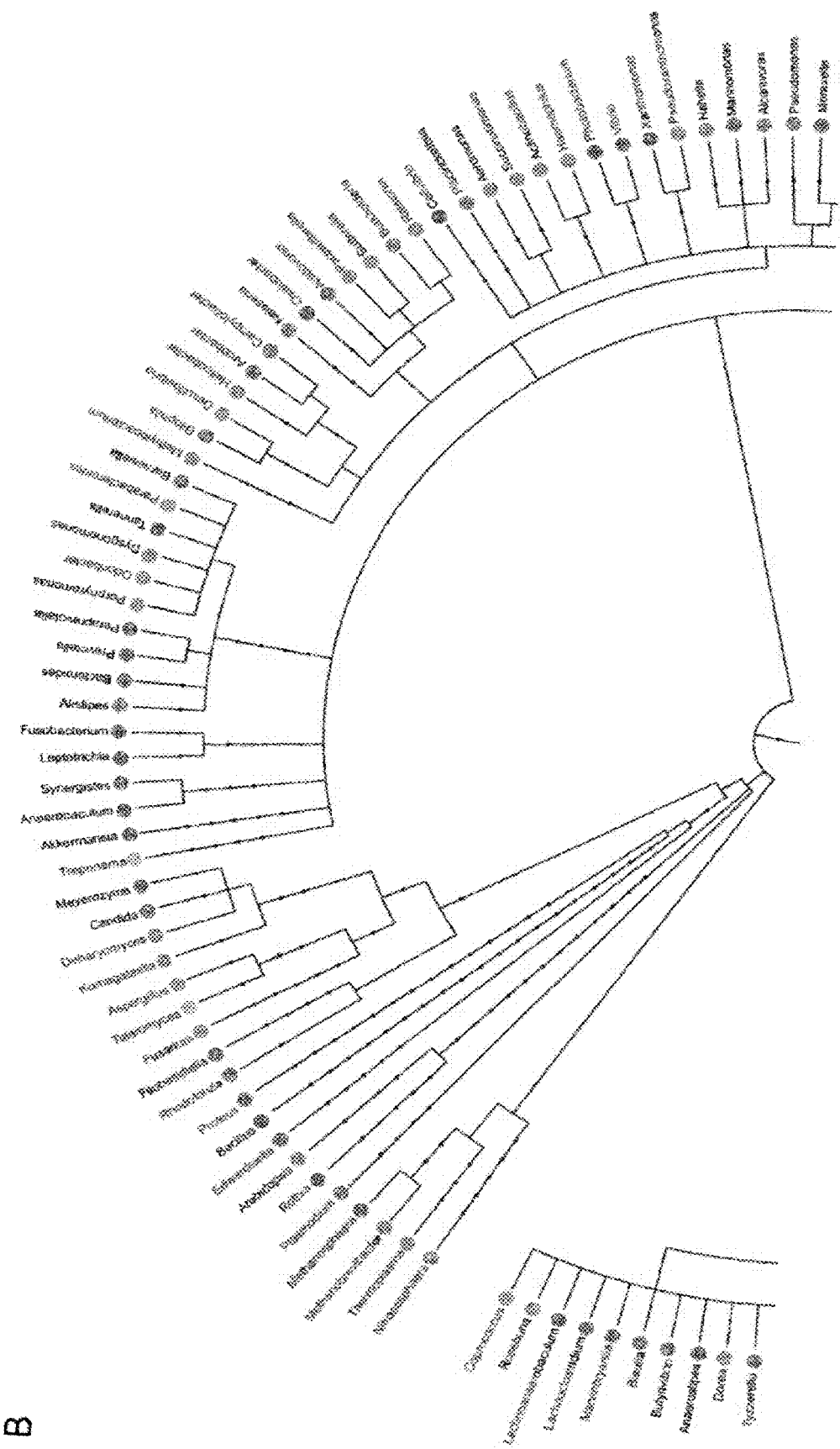
Figure 5:
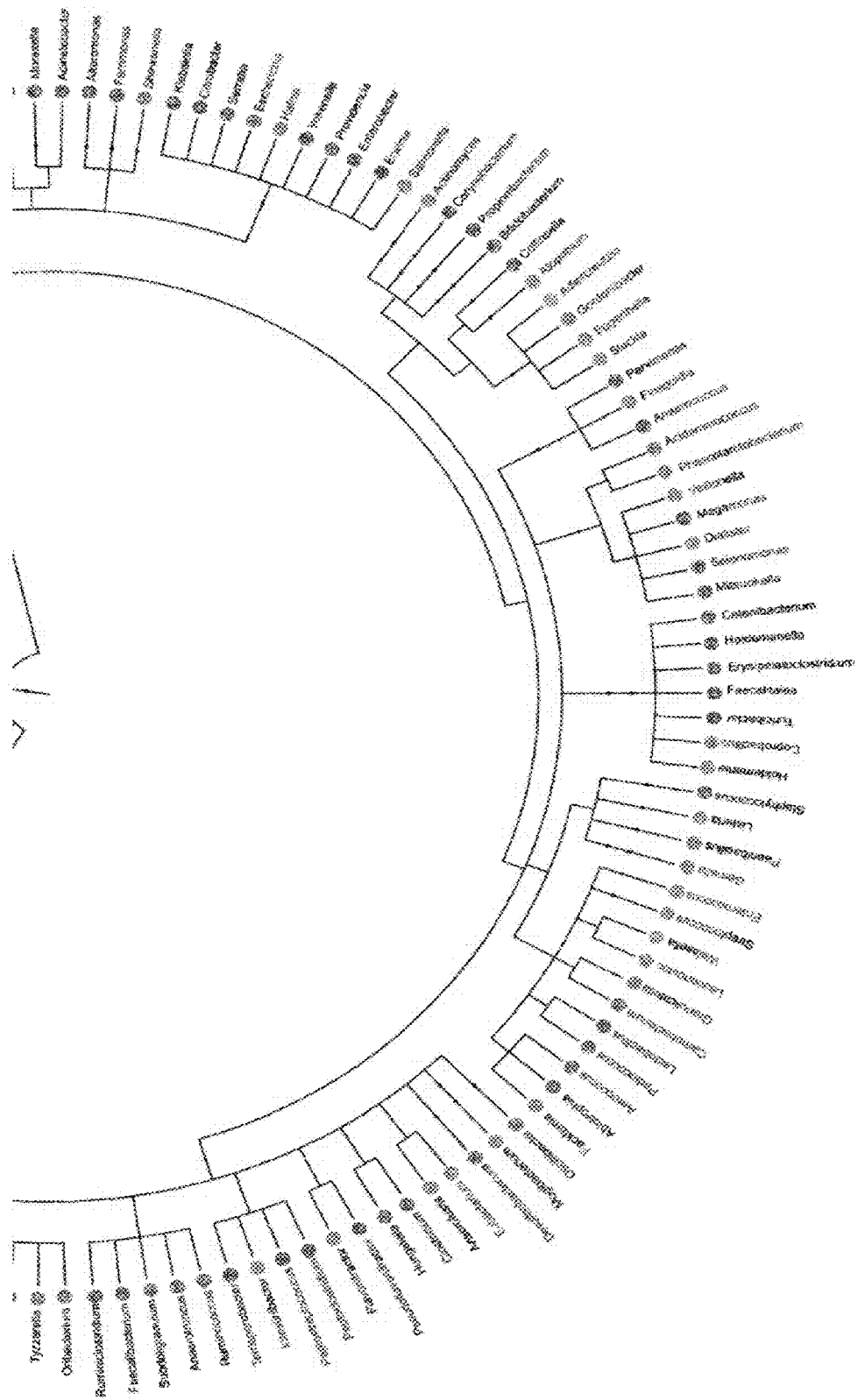

In order for this labeling approach to have broad applicability to a microbiome, the labeling is to be occurring across the various phyla and species represented within the microbiome samples. For instance, in some examples, in order to examine the representability of the $^{15}$N-labelled SILAMi, the SILAMi microbial composition was compared to the initial inoculum (Passage 0) using metaproteomics-based methods. This demonstrates if the SILAMi labeled proteins were representative of the initial population in the microbiota sample. Briefly, all the identified peptide sequences (i.e. $^{15}$N peptides in SILAMi and $^{14}$N peptides in Passage 0) were phylogenetically classified using Unipept, which assigns taxonomic information for peptides based on lowest common ancestor (LCA) algorithm, UniProt database and NCBI taxonomy [11]. As shown in FIG. 5, 16 of 18 microbial phyla (including those belong to Bacteria, Archaea, and Eukaryota kingdoms), and 138 of 142 genera that were detected in Passage 0 remained in the SILAMi reference (FIG. 5). This demonstrates that this labeling approach can efficiently label across all kingdoms as well as the majority of genera which are present in human microbiome samples. It will be appreciate that such an isotope-labelling standard may be used to perform accurate and reproducible metaproteomics.

Figure 2:
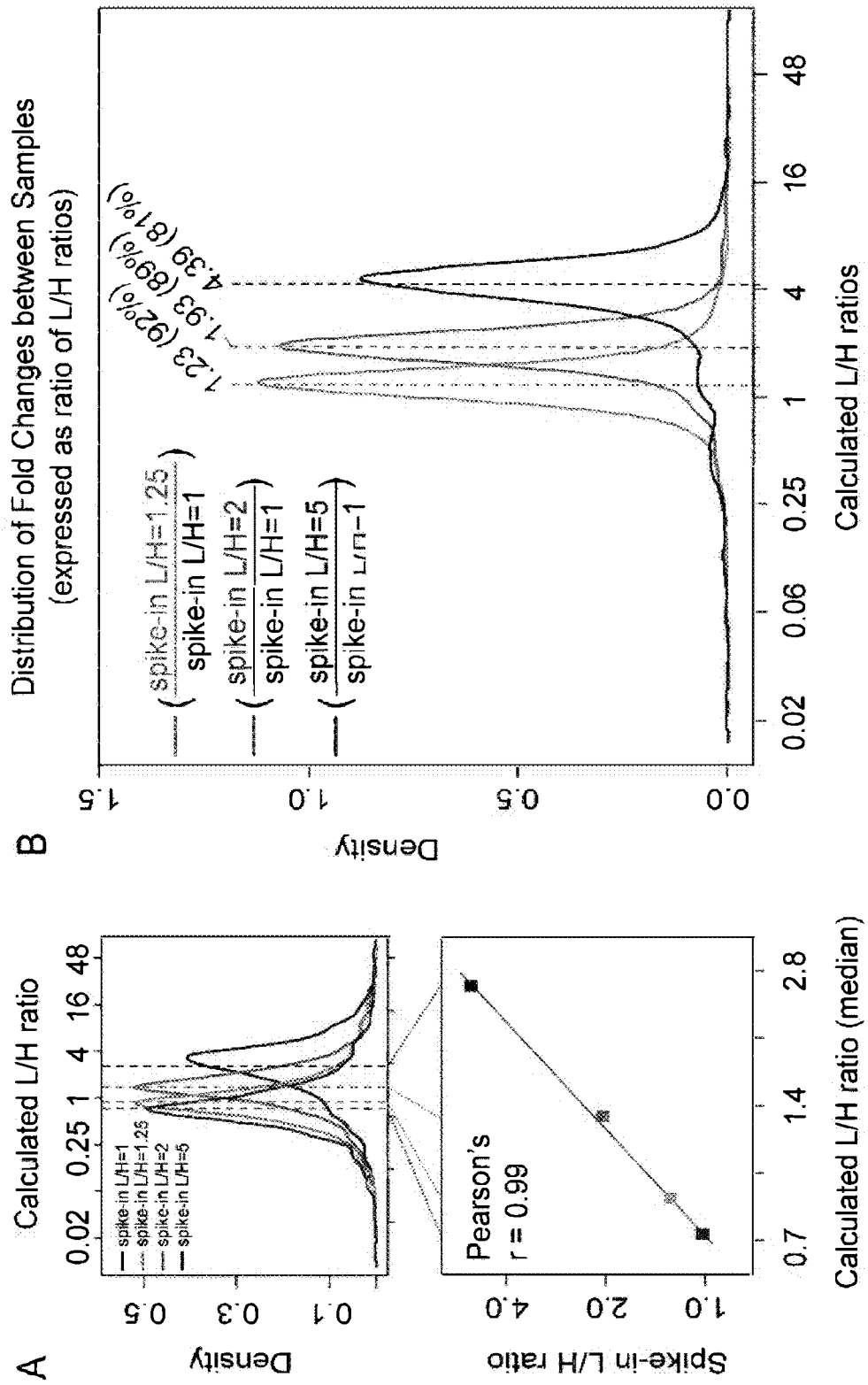
FIG. 2 describes the quantitation accuracy of the SILAMi-based metaproteomics. (A) Density plot showing the calculated L/H ratios of quantified protein groups in samples with different L/H spike-in ratios (1:1, 1.25:1, 2:1, and 5:1). Scatter plot shows the correlation between the calculated L/H protein ratios (median) and spike-in ratios. Pearson's r-value was indicated; (B) Density plot showing the distribution of fold changes when compared to the sample with 1:1 spike-in ratio. Log 2-transformed L/H ratios or fold changes were used for generating the density plots with a band width of 0.2. Dashed lines indicate median values. The percentage of proteins within two-fold difference to median was shown in the brackets.

In some examples, an isotope-labelled standard that has labelled 50% or more of the microbe population corresponding to an initial microbiota sample (an initial microbiota sample being the microbe population of the sample when initially obtained from the patient) may be used. However, it will be understood that the percentage of the microbe population of an initial microbiota sample that is to labelled to obtain an effective standard may vary depending upon the nature of the experiment (if only certain populations are desirable, such as the study of hydrogen sulfide producing bacteria in the study of inflammatory bowel disease).
Experiment 2: Accurate Ratio Measurement Using SILAMi Labeled Samples It was next tested whether accurate ratio measurement could be obtained using the SILAMi-based quantitative metaproteomics. Briefly, the same amount of SILAMi proteomes were spiked into different amounts of the unlabelled human gut metaproteome samples at L/H ratios of 1:1, 1.25:1, 2:1, and 5:1, respectively (e.g. FIG. 1A, 103). The mixtures were then processed for 4 hr gradient MS analysis on an Orbitrap Elite. A total of 6,943 unique peptide sequences corresponding to 4,014 protein groups were quantified and the L/H ratios 104 were calculated using Census. The distributions of calculated L/H ratios for all the quantified protein groups are shown in FIG. 2A, which demonstrated that the median L/H ratios were in great agreement with the spike-in ratios (Pearson's r=0.99). The fold change (FC) of each protein group between the four samples was then calculated by the "ratio of the L/H ratios" (FIG. 2B), which showed that narrow FC distributions were obtained, with 81-92% of the protein groups having less than two-fold difference to the median. Moreover, the median protein FCs (1.23, 1.93 and 4.39 folds; FIG. 2B) were in great agreement with the theoretical FC values (1.25, 2 and 5 folds, respectively). This demonstrates that metabolically labeled SILAMi microbiome can be used efficiently as an internal standard to reduce interexperiment and/or intraexperiment variability and optimize quantification in metaproteomics analysis. For instance, the use of an isotope-labelled standard for a microbiota population as described herein may identify false positives, changes in protein levels due to or experimental error or provide an indication if certain increases or reductions in the presence of certain proteins is a result of the preparation itself, or may be in fact due to a change in the microbiota as found in the original microbiota sample.

In summary, SILAMi represents a fast (3 days or less), efficient and cost-effective approach for generating metabolically labelled proteomes of intestinal microbial community, and allows accurate metaproteomic analysis of multiple samples with highly flexible experimental designs and implementations. SILAMi allows for highly standardized and quantitative analysis of the metaproteome, which will facilitate the use of metaproteomics analysis in the characterization of microbiome composition and function.

Figure 3:
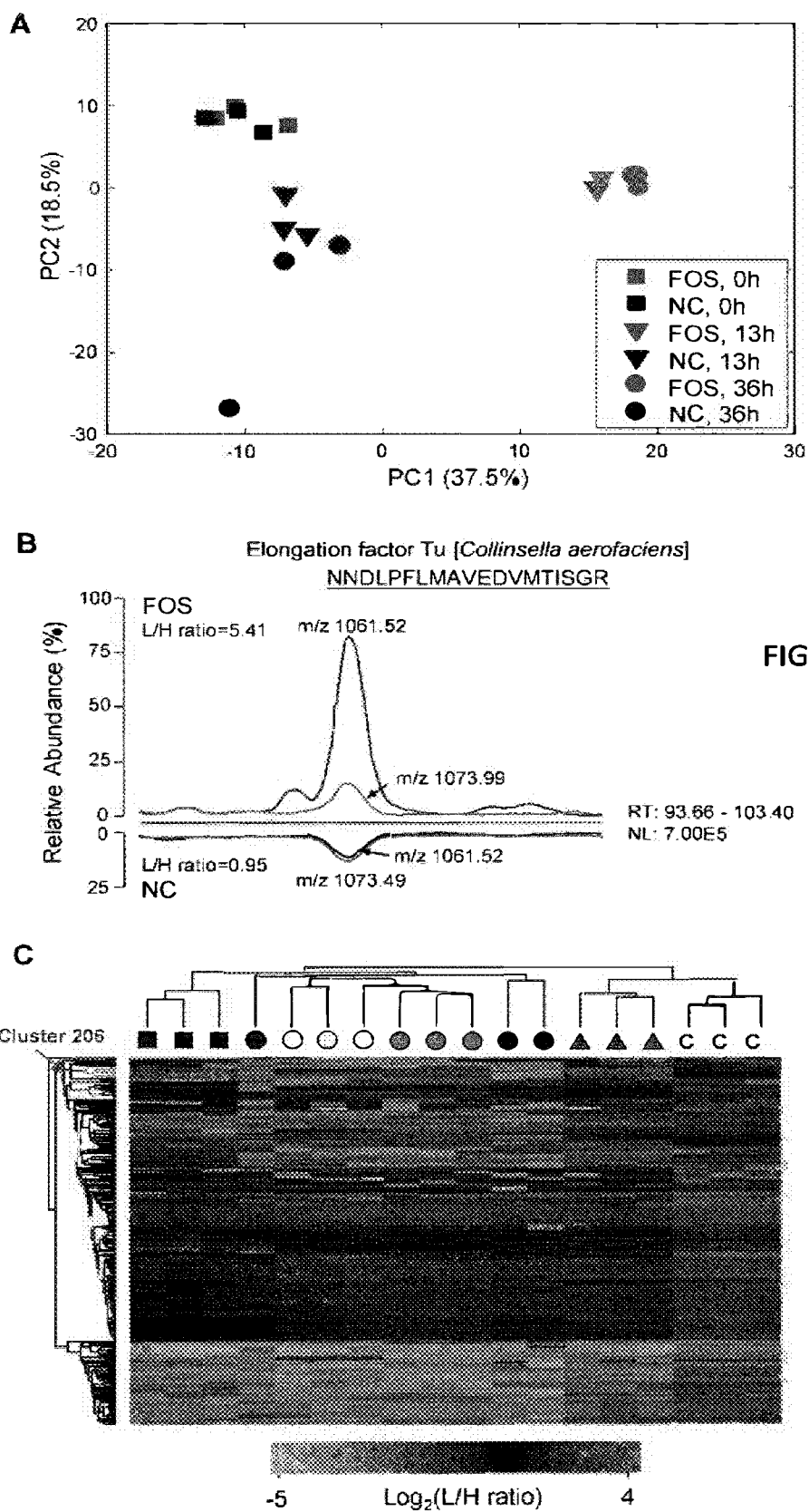
FIG. 3 illustrates examples of SILAMi-based quantitative metaproteomics for microbiota studies and the use of this technique for screening the effect of chemicals and/or compounds on microbiota protein expression overtime. (A) Principal component analysis score plot of FOS-mediated metaproteome changes. (B) Representative total ion currents (TICs) of quantified peptides of protein EF-Tu. Both heavy (red) and light (blue) are shown. (C) Heatmap of 246 microbial protein which significantly changed upon the supplementation of monosaccharides during in vitro cultivation. Both column and row clusterings were based on Euclidean distance. Blue square, N-acetyl glucosamine (GlcNAc); blue circle, glucose; yellow circle, galactose; green circle, mannose; red triangle, fucose; C, control. (D) Quantified proteins involved in bacterial fucose utilization pathway. Mean±SD was shown in the bar charts. DHAP, dihydroxyacetone phosphate; FucP, L-fucose:H+ symporter permease; FucM, L-fucose mutarotase; FucI, L-fucose isomerase; FucA, L-fuculose-1-phosphate aldolase; fucK, L-fuculokinase; FucO, L-1,2-propanediol oxidoreductase or lactaldehyde reductase. It will be understood that while microbiota samples were treated with monosaccharides, any compound could be used in this method to treat the microbiota samples and the subsequent effect on microbiome protein expression assessed.
Figure 3:
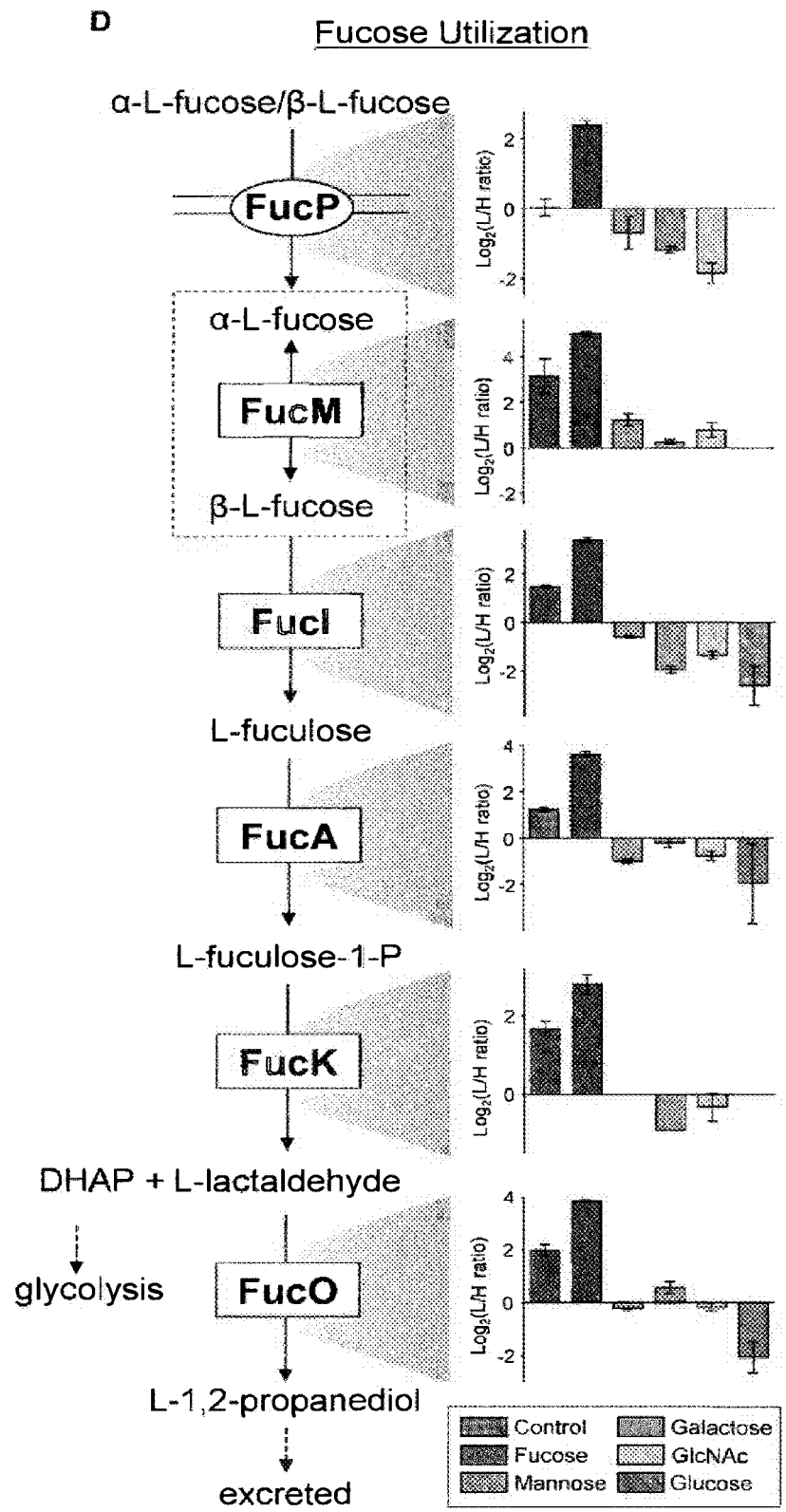

Example 1: Use of SILAMi to Assess Changes in a Microbiome as a Result of Treatment with a Compound As a proof-of-principle example demonstrating the application of SILAMi to assess changes in a microbiome treated with a compound overtime, the approach was applied for evaluating the effects of fructooligosaccharide (FOS), a known prebiotic, on the microbiota. Briefly, unlabelled intestinal microbiota were cultured in basal culture medium (BCM) with or without 10 mg/ml FOS for 13 and 36 hours. The proteomes extracted from each microbial culture were spiked with the labelled SILAMi reference and analyzed by mass spectrometry. Principal component analysis of the 2,280 quantified proteins showed that FOS markedly shifted the overall metaproteome along the first principal component (explains 37.5% of the total variance; FIG. 3A). 187 proteins were significantly changed, as shown in Table 3:

TABLE 3

187 identified protein groups altered by fructo-oligosacchride (FOS) treatment

| Protein_ID | Protein_name | Taxa |
| --- | --- | --- |
| YP_007784111.1 | LSU ribosomal protein L12P | Ruminococcus sp. SR1/5 |
| CBK99399.1 | pyruvate: ferredoxin (flavodoxin) oxidoreductase, homodimeric | Faecalibacterium prausnitzii L2-6 |
| EEU98313.1 | pyruvate synthase | Faecalibacterium prausnitzii A2-165 |
| EFQ07801.1 | pyruvate synthase | Faecalibacterium cf. prausnitzii KLE1255 |
| EFJ59195.1 | DNA-binding protein H-NS | Escherichia coli MS 200-1 |
| CBL23538.1 | Phosphotransferase system, HPr-related proteins | Ruminococcus obeum A2-162 |
| EET15673.1 | rubredoxin | Bacteroides sp. 4_3_47FAA |
| EHJ38221.1 | glutamate dehydrogenase, NAD-specific | Prevotella stercorea DSM 18206 |
| EEJ50816.1 | pyruvate, phosphate dikinase | Oribacterium sinus F0268 |
| EDR45788.1 | pyruvate, phosphate dikinase | Dorea formicigenerans ATCC 27755 |
| EFE12305.1 | rubredoxin | Clostridium sp. M62/1 |
| EDM52622.1 | rubredoxin | Eubacterium ventriosum ATCC 27560 |
| EEJ51973.1 | chaperonin GroL | Oribacterium sinus F0268 |
| CBK95920.1 | glutamate dehydrogenase (NADP) | Eubacterium siraeum 70/3 |

TABLE 3-continued 187 identified protein groups altered by fructo-oligosaccharide (FOS) treatment

| Protein_ID | Protein_name | Taxa |
|---|---|---|
| EDP26881.1 | Glu/Leu/Phe/Val dehydrogenase, dimerization domain protein | *Coprococcus eutactus* ATCC 27759 |
| EEC56529.1 | Glu/Leu/Phe/Val dehydrogenase, dimerization domain protein | *Bacteroides pectinophilus* ATCC 43243 |
| WP_008981262.1 | glutamate dehydrogenase | *Ruminococcaceae* bacterium D16 |
| EEO57674.1 | ribosomal protein L7/L12 | *Bacteroides* sp. 2_2_4 |
| EET14416.1 | ribosomal protein L7/L12 | *Bacteroides* sp. 4_3_47FAA |
| EDO55515.1 | ribosomal protein L7/L12 | *Bacteroides uniformis* ATCC 8492 |
| EKU90753.1 | acyl carrier protein | *Bacteroides oleiciplenus* YIT 12058 |
| EFV67501.1 | glyceraldehyde 3-phosphate dehydrogenase | *Bacteroides* sp. 3_1_40A |
| EDO52619.1 | glyceraldehyde-3-phosphate dehydrogenase, type I | *Bacteroides uniformis* ATCC 8492 |
| EDS13393.1 | glyceraldehyde-3-phosphate dehydrogenase, type I | *Bacteroides stercoris* ATCC 43183 |
| CBL23659.1 | Glutamate dehydrogenase/leucine dehydrogenase | *Ruminococcus obeum* A2-162 |
| CBK78198.1 | glyceraldehyde-3-phosphate dehydrogenase, type I | *Clostridium* cf. *saccharolyticum* K10 |
| EJZ69496.1 | glyceraldehyde-3-phosphate dehydrogenase, type I | *Lachnoanaerobaculum* sp. OBRC5-5 |
| EDO59009.1 | glyceraldehyde-3-phosphate dehydrogenase, type I | *Clostridium* sp. L2-50 |
| YP_007775284.1 | glyceraldehyde-3-phosphate dehydrogenase, type I | *Eubacterium siraeum* 70/3 |
| EEG49252.1 | hypothetical protein RUMHYD_01832 | *Blautia hydrogenotrophica* DSM 10507 |
| EDP25141.1 | hypothetical protein COPEUT_02635 | *Coprococcus eutactus* ATCC 27759 |
| EFE14625.1 | hypothetical protein CLOM621_05456 | *Clostridium* sp. M62/1 |
| WP_009005634.1 | hypothetical protein | *Clostridium* sp. D5 |
| EGG85123.1 | hypothetical protein HMPREF0992_00050 | *Lachnospiraceae* bacterium 6_1_63FAA |
| EEG49378.1 | ketol-acid reductoisomerase | *Blautia hydrogenotrophica* DSM 10507 |
| CBK94839.1 | chaperonin GroL | *Eubacterium rectale* M104/1 |
| EFC97322.1 | chaperonin GroL | *Clostridium hathewayi* DSM 13479 |
| EFU71919.1 | chaperone GroEL | *Campylobacter upsaliensis* JV21 |
| EDO56757.1 | Glu/Leu/Phe/Val dehydrogenase, dimerization domain protein | *Clostridium* sp. L2-50 |
| ACD05861.1 | Glutamate dehydrogenase (NADP(+)) | *Akkermansia muciniphila* ATCC BAA-835 |
| EEZ62164.1 | Glu/Leu/Phe/Val dehydrogenase, dimerization domain protein | *Slackia exigua* ATCC 700122 |
| EGW52698.1 | NADP-specific glutamate dehydrogenase | *Desulfovibrio* sp. 6_1_46AFAA |
| EHH00248.1 | hypothetical protein HMPREF9441_01482 | *Paraprevotella clara* YIT 11840 |
| EJZ66498.1 | hypothetical protein HMPREF9448_00677 | *Barnesiella intestinihominis* YIT 11860 |
| EMZ42216.1 | hypothetical protein HMPREF1091_01190 | *Atopobium minutum* 10063974 |
| EFI05647.1 | conserved hypothetical protein | *Bacteroides* sp. 1_1_14 |
| WP_010168870.1 | Rubrerythrin | *Epulopiscium* sp. 'N.t. morphotype B' |
| YP_007784205.1 | Rubrerythrin | *Ruminococcus* sp. SR1/5 |
| EID25347.1 | glyceraldehyde-3-phosphate dehydrogenase, type I | *Streptococcus pseudopneumoniae* ATCC BAA-960 |
| AGJ88568.1 | ADP-L-glycero-D-mannoheptose-6-epimerase | *Raoultella ornithinolytica* B6 |
| EFJ91797.1 | ADP-glyceromanno-heptose 6-epimerase | *Escherichia coli* MS 45-1 |
| EGB20520.1 | ribosomal protein S8 | *Clostridim symbiosum* WAL-14673 |
| EEG56094.1 | hypothetical protein CLOSTASPAR_01820 | *Clostridium asparagiforme* DSM 15981 |
| EHP50162.1 | reverse rubrerythrin-1 | *Clostridium perfringens* WAL-14572 |
| EGX68663.1 | triosephosphate isomerase | *Dorea formicigenerans* 4_6_53AFAA |
| EDM62185.1 | triose-phosphate isomerase | *Dorea longicatena* DSM 13814 |
| EHL68608.1 | triosephosphate isomerase | *Bacillus* sp. 7_6_55CFAA_CT2 |
| WP_009261992.1 | triosephosphate isomerase | *Lachnospiraceae* bacterium 9 1 43BFAA |
| EES65026.1 | butyryl-CoA dehydrogenase | *Fusobacterium varium* ATCC 27725 |
| CBK80400.1 | Acyl-CoA dehydrogenases | *Coprococcus catus* GD/7 |
| YP_007771689.1 | Acyl-CoA dehydrogenases | *Eubacterium rectale* DSM 17629 |
| EEG92096.1 | acyl-CoA dehydrogenase, C-terminal domain protein | *Roseburia inulinivorans* DSM 16841 |
| YP 007789048.1 | Acyl-CoA dehydrogenases | butyrate-producing bacterium SSC/2 |
| EDO58999.1 | acyl-CoA dehydrogenase, C-terminal domain protein | *Clostridium* sp. L2-50 |
| EGB17912.1 | acyl-CoA dehydrogenase, C-terminal domain protein | *Clostridium symbiosum* WAL-14673 |

TABLE 3-continued 187 identified protein groups altered by fructo-oligosacchride (FOS) treatment

| Protein_ID | Protein_name | Taxa |
| --- | --- | --- |
| WP_008981913.1 | acyl-CoA dehydrogenase | *Ruminococcaceae* bacterium D16 |
| CBL15057.1 | hypothetical protein RBR_06960 | *Ruminococcus bromii* L2-63 |
| EEG90243.1 | acetyl-CoA C-acetyltransferase | *Coprococcus comes* ATCC 27758 |
| EGB17915.1 | acetyl-CoA C-acetyltransferase | *Clostridium symbiosum* WAL-14673 |
| EEG35102.1 | pyridoxal-phosphate dependent TrpB-like enzyme | *Eubacterium hallii* DSM 3353 |
| EGB18784.1 | cell wall-binding repeat protein | *Clostridium symbiosum* WAL-14673 |
| ADG61750.1 | chaperonin protein Cpn60 | *Moraxella catarrhalis* BBH18 |
| EFU70513.1 | chaperone GroEL | *Arcobacter butzleri* JV22 |
| WP_010167160.1 | molecular chaperone GroEL | *Epulopiscium* sp. 'N.t. morphotype B' |
| YP_007849205.1 | chaperonin GroL | *Clostridium* cf. *saccharolyticum* K10 |
| EGA92696.1 | hypothetical protein HMPREF9474_03417 | *Clostridium symbiosum* WAL-14163 |
| CBK80101.1 | LSU ribosomal protein L10P | *Coprococcus catus* GD/7 |
| YP_007785100.1 | Formate-tetrahydrofolate ligase | *Ruminococcus* sp. SR1/5 |
| EES75500.1 | formate-tetrahydrofolate ligase | *Ruminococcus* sp. 5_1_39BFAA |
| CBL24477.1 | Formate-tetrahydrofolate ligase | *Ruminococcus obeum* A2-162 |
| WP_009644236.1 | rubrerythrin domain protein | *Mogibacterium* sp. CM50 |
| EGB17993.1 | chaperonin GroL | *Clostridium symbiosum* WAL-14673 |
| EDY32295.1 | triose-phosphate isomerase | *Ruminococcus lactaris* ATCC 29176 |
| YP_007786820.1 | triosephosphate isomerase | *Ruminococcus torques* L2-14 |
| ACV56754.1 | ribosomal protein S13 | *Eggerthella lenta* DSM 2243 |
| EEX17882.1 | glutamate dehydrogenase, NAD-specific | *Prevotella veroralis* F0319 |
| EGN46805.1 | 50S ribosomal protein L7/L12 | Lachnospiraceae bacterium 2_1_58FAA |
| EEG51161.1 | Rubrerythrin, partial | *Clostridium asparagiforme* DSM 15981 |
| EEX22906.1 | formate--tetrahydrofolatel igase, partial | *Blautia hansenii* DSM 20583 |
| YP_007782188.1 | Glutamate dehydrogenase/leucine dehydrogenase | *Ruminococcus* sp. SR1/5 |
| EEG47401.1 | Glu/Leu/Phe/Val dehydrogenase, dimerization domain protein | *Blautia hydrogenotrophica* DSM 10507 |
| EDQ97591.1 | Glu/Leu/Phe/Val dehydrogenase, dimerization domain protein | *Intestinibacter bartlettii* DSM 16795 |
| YP_007768517.1 | Glutamate dehydrogenase/leucine dehydrogenase | *Coprococcus catus* GD/7 |
| YP_007830561.1 | Glutamate dehydrogenase/leucine dehydrogenase | *Roseburia intestinalis* M50/1 |
| EHP49125.1 | hypothetical protein HMPREF9476_01168 | *Clostridium perfringens* WAL-14572 |
| EFW89087.1 | Glu/Leu/Phe/Val dehydrogenase, dimerization domain protein | *Streptococcus equinus* ATCC 9812 |
| YP_007839796.1 | glutamate dehydrogenase (NADP) | *Eubacterium siraeum* V10Sc8a |
| EEG31752.1 | Glu/Leu/Phe/Val dehydrogenase, dimerization domain protein | *Clostridium methylpentosum* DSM 5476 |
| EDS03463.1 | glutamate dehydrogenase, NAD-specific | *Alistipes putredinis* DSM 17216 |
| EKA95101.1 | NADP-specific glutamate dehydrogenase | *Proteus mirabilis* WGLW6 |
| EEG86298.1 | Glu/Leu/Phe/Val dehydrogenase, dimerization domain protein | *Proteus penneri* ATCC 35198 |
| EES78421.1 | hypothetical protein RSAG_00378 | *Ruminococcus* sp. 5_1_39BFAA |
| EHG28402.1 | hypothetical protein HMPREF9478_01803 | *Enterococcus saccharolyticus* 30_1 |
| EHO80265.1 | hypothetical protein HMPREF0402_02090 | *Fusobacterium ulcerans* 12-1B |
| CBK99448.1 | Electron transfer flavoprotein, beta subunit | *Faecalibacterium prausnitzii* L2-6 |
| EHJ31916.1 | electron transfer flavoprotein subunit beta | *Peptoclostridium difficile* 002-P50-2011 |
| EFB77236.1 | electron transfer flavoprotein domain protein | *Subdoligranulum variabile* DSM 15176 |
| WP_020989365.1 | electron transfer flavoprotein beta subunit | *Ruminococcaceae* bacterium D16 |
| YP_008664299.1 | glutamate dehydrogenase | *Adlercreutzia equolifaciens* DSM 19450 |
| YP_007801881.1 | glutamate dehydrogenase (NADP) | *Gordonibacter pamelaeae* 7-10-1-b |
| CBL18303.1 | glutamate dehydrogenase (NADP) | *Ruminococcus champanellensis* 18P13 = JCM 17042 |
| WP_019893516.1 | glutamate dehydrogenase | *Allobaculum stercoricanis* |
| EMZ41672.1 | glutamate dehydrogenase (NADP+) | *Atopobium minutum* 10063974 |
| YP_007837627.1 | glutamate dehydrogenase (NADP) | *Faecalibacterium prausnitzii* L2-6 |
| EDM50401.1 | Glu/Leu/Phe/Val dehydrogenase, dimerization domain protein | *Eubacterium ventriosum* ATCC 27560 |
| EFF68264.1 | Glu/Leu/Phe/Val dehydrogenase, dimerization domain protein | *Butyrivibrio crossotus* DSM 2876 |
| EEG37302.1 | Glu/Leu/Phe/Val dehydrogenase, dimerization domain protein | *Eubacterium hallii* DSM 3353 |
| EFR58785.1 | glutamate dehydrogenase, NAD-specific | *Alistipes* sp. HGB5 |
| CBK64456.1 | glutamate dehydrogenase (NAD) | *Alistipes shahii* WAL 8301 |

TABLE 3-continued 187 identified protein groups altered by fructo-oligosacchride (FOS) treatment

| Protein_ID | Protein_name | Taxa |
| --- | --- | --- |
| EFW05566.1 | Glutamate:leucine:phenylalanine:valine dehydrogenase | *Coprobacillus* sp. 29_1 |
| CBL26527.1 | Glutamate dehydrogenase/leucine dehydrogenase | *Ruminococcus torques* L2-14 |
| EET58217.1 | Glu/Leu/Phe/Val dehydrogenase, dimerization domain protein | *Marvinbryantia formatexigens* DSM 14469 |
| EFK29209.1 | Glu/Leu/Phe/Val dehydrogenase, dimerization domain protein | *Lactobacillus plantarum* subsp. *plantarum* ATCC 14917 |
| EEQ44915.1 | NADP-specific glutamate dehydrogenase | *Candida albicans* WO-1 |
| WP_009733626.1 | glutamate dehydrogenase | *Bilophila* sp. 4_1_30 |
| CBK74255.1 | glutamate dehydrogenase (NADP) | *Butyrivibrio fibrisolvens* 16/4 |
| EFC93334.1 | Glu/Leu/Phe/Val dehydrogenase, dimerization domain protein | *Methanobrevibacter smithii* DSM 2374 |
| EFI84299.1 | Glu/Leu/Phe/Val dehydrogenase, dimerization domain protein | *Listeria grayi* DSM 20601 |
| EEB34074.1 | Glu/Leu/Phe/Val dehydrogenase, dimerization domain protein | *Desulfovibrio piger* ATCC 29098 |
| EJF41864.1 | Glu/Leu/Phe/Val dehydrogenase, dimerization domain protein | *Actinomyces massiliensis* F0489 |
| YP_007781565.1 | Glutamate dehydrogenase/leucine dehydrogenase | *Ruminococcus bromii* L2-63 |
| EHL05236.1 | NAD(P)-specific glutamate dehydrogenase | *Desulfitobacterium hafniense* DP7 |
| EKX90337.1 | Glu/Leu/Phe/Val dehydrogenase, dimerization domain protein | *Corynebacterium durum* F0235 |
| EGG79390.1 | NADP-specific glutamate dehydrogenase | Lachnospiraceae bacterium 6_1_63FAA |
| EJU21607.1 | glutamate dehydrogenase, NAD-specific | *Mogibacterium* sp. CM50 |
| EGX98849.1 | glutamate dehydrogenase | *Lactobacillus ruminis* ATCC 25644 |
| WP_002582046.1 | glutamate dehydrogenase | *Clostridium butyricum* |
| EHN61579.1 | Glu/Leu/Phe/Val dehydrogenase, dimerization domain protein | *Listeria innocua* ATCC 33091 |
| YP_004374626.1 | cryptic glutamate dehydrogenase | *Carnobacterium* sp. 17-4 |
| CBL42834.1 | Glutamate dehydrogenase/leucine dehydrogenase | butyrate-producing bacterium SS3/4 |
| EES65252.1 | translation elongation factor Ts | *Fusobacterium varium* ATCC 27725 |
| EEG47205.1 | formate -- tetrahydrofolate ligase, partial | *Blautia hydrogenotrophica* DSM 10507 |
| EFV22449.1 | rubredoxin | *Anaerostipes* sp. 3_2_56FAA |
| EHO34579.1 | hypothetical protein HMPREF0995_01217 | Lachnospiraceae bacterium 7 1 58FAA |
| CBL23222.1 | Carbon dioxide concentrating mechanism/carboxysome shell protein | *Ruminococcus obeum* A2-162 |
| EHI57300.1 | hypothetical protein HMPREF9473_04409 | *Clostridium hathewayi* WAL-18680 |
| CBL25604.1 | Carbon dioxide concentrating mechanism/carboxysome shell protein | *Ruminococcus torques* L2-14 |
| YP_007783749.1 | Carbon dioxide concentrating mechanism/carboxysome shell protein | *Ruminococcus* sp. SR1/5 |
| EFV41475.1 | propanediol utilization protein PduA | Enterobacteriaceae bacterium 9_2_54FAA |
| EEG37602.1 | BMC domain protein | *Eubacterium hallii* DSM 3353 |
| EEB47897.1 | ribosomal protein S4 | *Providencia alcalifaciens* DSM 30120 |
| EEQ62196.1 | ribosomal protein S5 | Clostridiales bacterium 1_7_47FAA |
| WP_009461300.1 | 30S ribosomal protein S5 | Lachnospiraceae bacterium 2_1_46FAA |
| EEF93821.1 | translation elongation factor Tu | *Catenibacterium mitsuokai* DSM 15897 |
| EEY85351.1 | translation elongation factor Tu | *Acinetobacter radioresistens* SH164 |
| EFG16453.1 | transporter, MotA/TolQ/ExbB proton channel family protein | *Bacteroides vulgatus* PC510 |
| EFV65278.1 | fructose-bisphosphate aldolase | *Bacteroides* sp. 3_1_40A |
| EEC95866.1 | fructose-1,6-bisphosphate aldolase, class II | *Parabacteroides johnsonii* DSM 18315 |
| CBK74269.1 | phosphoenolpyruvate carboxykinase (ATP) | *Butyrivibrio fibrisolvens* 16/4 |
| EEU32089.1 | chaperonin | *Fusobacterium nucleatum* subsp. vincentii 3_1_36A2 |
| WP_018590022.1 | molecular chaperone GroEL | *Terrisporobacter glycolicus* |
| EFS23154.1 | chaperonin GroL | *Fusobacterium necrophorum* D12 |
| EFY04737.1 | B12 binding domain protein | *Phascolarctobacterium succinatutens* YIT 12067 |
| EEQ65050.1 | elongation factor Tu | *Lactobacillus paracasei* subsp. *paracasei* 8700:2 |
| CBL22274.1 | phosphoenolpyruvate carboxykinase (ATP) | *Ruminococcus obeum* A2-162 |
| CBL01371.1 | phosphoenolpyruvate carboxykinase (ATP) | *Faecalibacterium prausnitzii* SL3/3 |

TABLE 3-continued

187 identified protein groups altered by fructo-oligosacchride (FOS) treatment

| Protein_ID | Protein_name | Taxa |
|---|---|---|
| EDM63411.1 | phosphoenolpyruvate carboxykinase (ATP) | *Dorea longicatena* DSM 13814 |
| EEA80919.1 | phosphoenolpyruvate carboxykinase (ATP) | *Tyzzerella nexilis* DSM 1787 |
| EFV68881.1 | plasminogen binding protein | *Bacteroides* sp. 3_1_40A |
| EEO45868.1 | tetratricopeptide repeat protein | *Bacteroides dorei* 5_1_36/D4 |
| EGN48017.1 | 50S ribosomal protein L7/L12 | Lachnospiraceae bacterium 3_1_57FAA_CTI |
| EGX69049.1 | elongation factor Tu | *Collinsella tanakaei* YIT 12063 |
| EEP44307.1 | translation elongation factor Tu | *Collinsella intestinalis* DSM 13280 |
| ACV51606.1 | translation elongation factor Tu | *Atopobium parvulum* DSM 20469 |
| YP_002294143.1 | autonomous glycyl radical cofactor GrcA | *Escherichia coli* SE11 |
| EER73923.1 | translation elongation factor Tu | *Weissella paramesenteroides* ATCC 33313 |
| EES64428.1 | DNA-binding protein, YbaB/EbfC family | *Fusobacterium varium* ATCC 27725 |
| EFK66259.1 | phosphoenolpyruvate-protein phosphotransferase | *Escherichia coli* MS 124-1 |
| EEX68873.1 | ATP synthase F1, beta subunit | *Mitsuokella multacida* DSM 20544 |
| EFY04736.1 | methylmalonyl-CoA mutase domain protein | *Phascolarctobacterium succinatutens* YIT 12067 |
| ACV56138.1 | ribosomal protein L2 | *Eggerthella lenta* DSM 2243 |
| EFY04939.1 | ribosomal protein S3 | *Phascolarctobacterium succinatutens* YIT 12067 |
| EHR32371.1 | ATP synthase subunit beta | *Megamonas funiformis* YIT 11815 |
| EBA39887.1 | translation elongation factor Tu | *Collinsella aerofaciens* ATCC 25986 |
| EES64070.1 | glyceraldehyde-3-phosphate dehydrogenase, type I | *Fusobacterium varium* ATCC 27725 |
| EBA39912.1 | ribosomal protein L7/L12 | *Collinsella aerofaciens* ATCC 25986 |
| EGX68988.1 | 30S ribosomal protein S10 | *Collinsella tanakaei* YIT 12063 |

Figure 6:
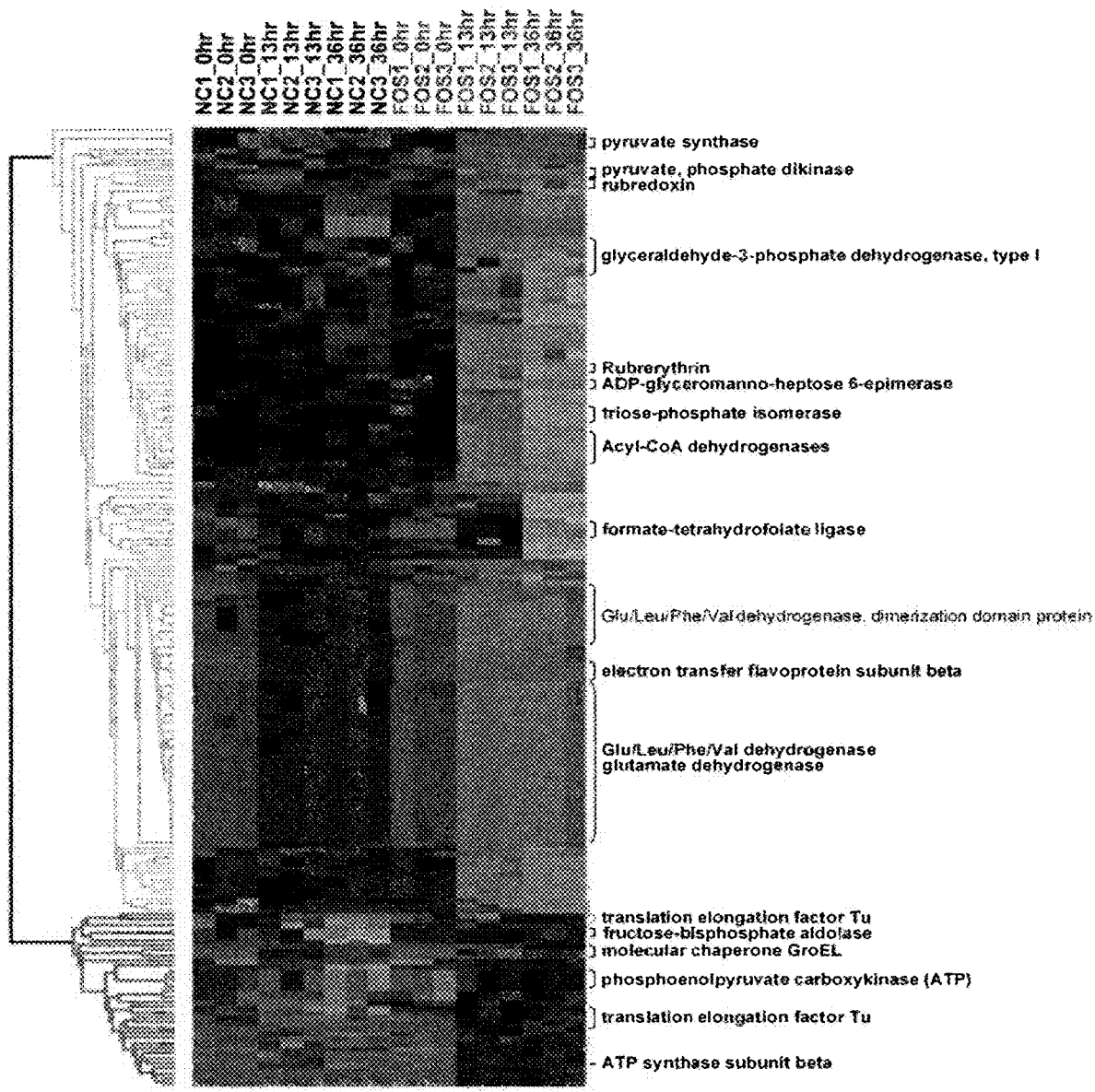
FIG. 6 represents a heat map of the 187 identified protein groups altered by fructooligosaccharide (FOS) treatment. Complete protein names are listed in Table 3; a few proteins of interest are indicated. The clustering of rows was generated based on Euclidean distance in Perseus. It will be understood that while this example demonstrates changes from treatment with FOS, a heatmap of changes could be generated from microbiome protein changes following treatment with any compound using the methods described herein.
Figure 7:
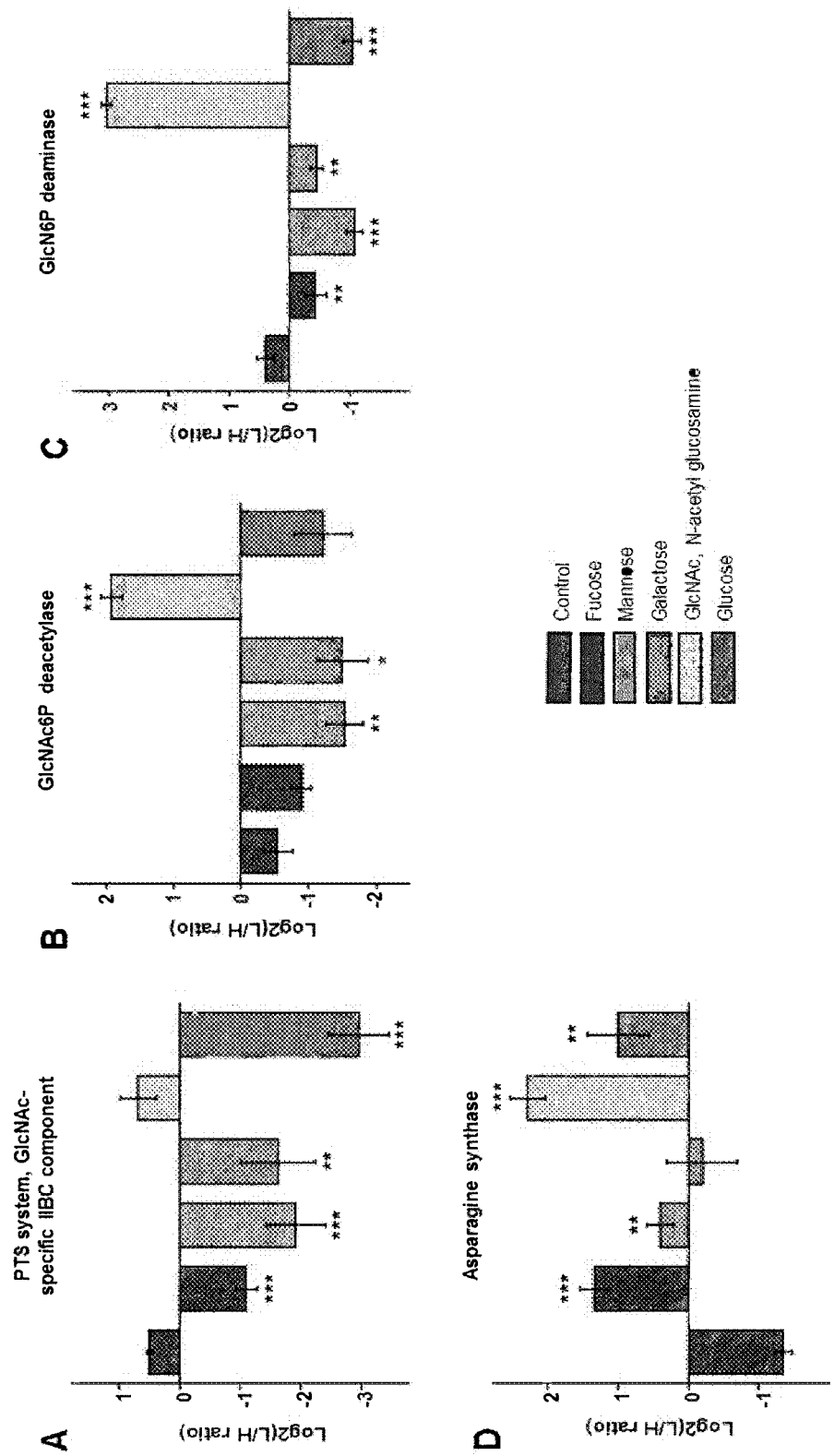
FIG. 7 illustrates the influence of monosaccharides on the relative abundance of N-acetyl glucosamine-degrading related proteins in human microbiome samples. Log 2-transformed L/H ratios are shown and expressed as mean±SD. A two sample t-test was used to compare differences between the non-treated control group (n=3) and the treated sample (n=3). *P<0.05, P<0.01, *P<0.001.

Among the identified 187 significantly changed proteins (FIG. 6), eight orthologs of the translation elongation factor Tu (EF-Tu) from different bacterial species were found to be increased by FOS (up to 6 fold, FIG. 3B). Additionally, nine orthologs of glyceraldehyde-3-phosphate dehydrogenase protein from different species were also quantified, among which eight isoforms were decreased while the one from *Fusobacterium varium* was increased. It also found that the proteins involved in endotoxin synthesis (eg., ADP-glycero-manno-heptose 6-epimerase) were decreased, suggesting an inhibiting role of FOS on potential endotoxin-producing pathogens in the intestinal tract. This demonstrates that SILAMi can be used to quantitatively assess changes in metaproteomic expression following treatment with a compound and that these changes can indicate specific pathways and functions that are effected by the treatment of these compounds. This approach could be used to identify therapeutic targets, diagnostics and assess treatment response.

Finally, it was tested whether the SILAMi labelled-standard could be used to distinguish the effects of different monosaccharides on the microbiota. It will be understood that monosaccharides are used herein as an example of a compound that may have an effect on the microbiota. However, other compounds that have be introduced to a microbiota sample or to a subject of which a microbiota sample has been obtained, that may impact the microbiota, may be similarly analyzed as described herein.

Overall, 18 samples cultured with or without 2.5 g/L of each monosaccharide (N-acetyl glucosamine or GlcNAc, mannose, galactose, fucose, or glucose) were analyzed, by SILAMi-based metaproteomics which led to 3,158 quantified proteins. Two hundred and forty-six protein groups were identified as being differentially abundant as compared to the non-treated control group (Table 4):

TABLE 4 the two hundred and forty-six protein groups were identified as being differentially abundant as compared to the non-treated control group following metaproteomics with SILAMi.

| Protein_ID | Protein_name | taxonomy |
|---|---|---|
| EFY04736.1 | methylmalonyl-CoA mutase domain protein | *Phascolarctobacterium succinatutens* YIT 12067 |
| EFF50472.1 | chaperonin GroL | *Bacteroides ovatus* SD CMC 3f |
| EFG25764.1 | methylmalonyl-CoA mutase | *Veillonella* sp. 6_1_27 |
| EFG19106.1 | pyruvate, phosphate dikinase | *Bacteroides vulgatus* PC510 |
| EFD84126.1 | lactaldehyde reductase | *Klebsiella* sp. 1_1_55 |
| AGJ89383.1 | L-fucose isomerase | *Raoultella ornithinolytica* B6 |
| EFK03838.1 | arabinose isomerase | *Escherichia coli* MS 182-1 |
| EKN23949.1 | hypothetical protein HMPREF1059_02856 | *Parabacteroides distasonis* CL09T03C24 |
| EEZ28128.1 | pyruvate, phosphate dikinase | *Bacteroides* sp. 2_1_16 |
| EET14319.1 | phosphoenolpyruvate carboxykinase (ATP) | *Bacteroides* sp. 4_3_47FAA |
| EET60019.1 | ribosomal protein L7 L12 | *Marvinbryantia formatexigens* DSM 14469 |
| EFK61747.1 | hypothetical protein HMPREF9008_02015 | *Parabacteroides* sp. 20_3 |

TABLE 4-continued the two hundred and forty-six protein groups were identified as being differentially abundant as compared to the non-treated control group following metaproteomics with SILAMi.

| Protein_ID | Protein_name | taxonomy |
| --- | --- | --- |
| EKN23143.1 | hypothetical protein HMPREF1059_03287 | *Parabacteroides distasonis* CL09T03C24 |
| YP_002292782.1 | hypothetical protein ECSE_1507 | *Escherichia coli* SE11 |
| EEJ51224.1 | arabinose isomerase | *Oribacterium sinus* F0268 |
| EFJ64969.1 | lactaldehyde reductase | *Escherichia coli* MS 175-1 |
| EEG94073.1 | ribosomal protein L7 L12 | *Roseburia inulinivorans* DSM 16841 |
| EFG23247.1 | translation elongation factor G | *Veillonella* sp. 3_1_44 |
| YP_003350581.1 | L-fuculose-1-phosphate aldolase | *Escherichia coli* SE15 |
| EHM50183.1 | glutamine-fructose-6-phosphate transaminase | *Yokenella regensburgei* ATCC 43003 |
| YP_002294335.1 | L-fuculose phosphate aldolase | *Escherichia coli* SE11 |
| EHP45389.1 | phosphoenolpyruvate carboxykinase [ATP] | *Odoribacter laneus* YIT 12061 |
| EFY05605.1 | translation elongation factor G | *Phascolarctobacterium succinatutens* YIT 12067 |
| EEA80457.1 | hypothetical protein CLONEX_03662 | *Tyzzerella nexilis* DSM1 787 |
| EEO62927.1 | Xaa-His dipeptidase | *Bacteroides* sp. 9_1_42FAA |
| EFK60382.1 | phosphoenolpyruvate carboxykinase (ATP) | *Parabacteroides* sp. 20_3 |
| EDV01624.1 | ribosomal protein S12 | *Bacteroides coprocola* DSM 17136 |
| EFU58095.1 | L-fucose:H+ symporter permease | *Escherichia coli* MS 16-3 |
| EFD04604.1 | ribosomal protein S12 | *Peptostreptococcus anaerobius* 653-L |
| EBA39920.1 | ribosomal protein S12 | *Collinsella aerofaciens* ATCC 25986 |
| EHL76277.1 | 30S ribosomal protein S12 | *Bacillus smithii* 7_3_47FAA |
| EFG23245.1 | ribosomal protein S12 | *Veillonella* sp. 3_1_44 |
| EEU51870.1 | phosphoglycerate kinase | *Parabacteroides* sp. D13 |
| EEZ25115.1 | phosphoglycerate kinase | *Bacteroides* sp. 2_1_16 |
| EGB19009.1 | pyruvate, phosphate dikinase | *Clostridium symbiosum* WAL-14673 |
| EHP48549.1 | pyruvate, phosphate dikinase | *Clostridium perfringens* WAL-14572 |
| EFU52197.1 | glutamine-fructose-6-phosphate transaminase (isomerizing) | *Escherichia coli* MS 153-1 |
| CDM03263.1 | SSU ribosomal protein S11p (S14e) | *Bacteroides xylanisolvens* SD CC 1b |
| EEU49302.1 | tetratricopeptide repeat protein | *Parabacteroides* sp. D13 |
| EDM19917.1 | transporter, MotA TolQ ExbB proton channel family protein | *Bacteroides caccae* ATCC 43185 |
| EHE95587.1 | ketol-acid reductoisomerase | *Clostridium citroniae* WAL-17108 |
| EDM88222.1 | pyruvate, phosphate dikinase | *Ruminococcus obeum* ATCC 29174 |
| EFC98279.1 | pyruvate, phosphate dikinase | *Clostridium hathewayi* DSM 13479 |
| EHI58090.1 | pyruvate, phosphate dikinase | *Clostridium hathewayi* WAL-18680 |
| EFV23852.1 | hypothetical protein HMPREF1011_00311 | *Anaerostipes* sp. 3_2_56FAA |
| ACA17149.1 | pyruvate, phosphate dikinase | *Methylobacterium* sp. 4-46 |
| EDS09607.1 | pyruvate, phosphate dikinase | *Anaerotruncus colihominis* DSM 17241 |
| EFJ97558.1 | glycerol-3-phosphate dehydrogenase, anaerobic, A subunit | *Escherichia coli* MS 115-1 |
| EDN88029.1 | hypothetical protein PARMER 00607 | *Parabacteroides merdae* ATCC 43184 |
| EHP67661.1 | succinate dehydrogenase flavoprotein subunit | *Escherichia coli* 4_1_47FAA |
| EFK60341.1 | tetratricopeptide repeat protein | *Parabacteroides* sp. 20_3 |
| EFK61507.1 | malate dehydrogenase, NAD-dependent | *Parabacteroides* sp. 20_3 |
| EEQ57746.1 | pyruvate, phosphate dikinase | *Clostridiales bacterium* 1_7_47FAA |
| EDP13424.1 | hypothetical protein CLOBOL_06339 | *Clostridium bolteae* ATCC BAA-613 |
| EEZ23361.1 | rubredoxin | *Bacteroides* sp. 3_1_33FAA |
| EET16778.1 | trigger factor | *Bacteroides* sp. 4_3_47FAA |
| EEY84376.1 | TonB-linked outer membrane protein, SusC RagA family | *Bacteroides* sp. 2_1_33B |
| B617Z9.1 | Succinyl-CoA ligase [ADP-forming] subunit beta | *Escherichia coli* SE11 |
| EEZ25084.1 | fructose-1,6-bisphosphate aldolase, class II | *Bacteroides* sp. 2_1_16 |
| AGH75904.1 | glycerol kinase | *Xanthomonas axonopodis* Xac29-1 |
| EEZ20650.1 | malate dehydrogenase, NAD-dependent | *Bacteroides* sp. 3_1_33FAA |
| EGN42283.1 | phosphoenolpyruvate carboxykinase | *Lachnospiraceae bacterium* 1_1_57FAA |
| EEU51305.1 | rubredoxin | *Parabacteroides* sp. D13 |
| YP_007794708.1 | Rubrerythrin | *Bacteroides xylanisolvens* XB1A |
| EFI88374.1 | transcriptional regulator, PadR family | *Escherichia coli* MS 196-1 |
| EET17854.2 | fructose-1,6-bisphosphate aldolase, class II | *Bacteroides* sp. 4_3_47FAA |
| EFU52050.1 | glycerol kinase | *Escherichia coli* MS 153-1 |
| EEH85689.1 | L-asparaginase | *Escherichia* sp. 3_2_53FAA |
| EGB18784.1 | cell wall-binding repeat protein | *Clostridium symbiosum* WAL-14673 |
| EEH89155.1 | glycerol kinase | *Escherichia* sp. 3_2_53FAA |
| EEO47368.1 | succinate dehydrogenase flavoprotein subunit | *Bacteroides dorei* 5_1_36 D4 |
| EFR55977.1 | succinate dehydrogenase flavoprotein subunit | *Bacteroides fragilis* 3_1_12 |
| EFV69103.1 | fumarate reductase flavoprotein subunit | *Bacteroides* sp. 3_1_40A |
| EFK60272.1 | succinate dehydrogenase flavoprotein subunit | *Parabacteroides* sp. 20_3 |
| YP_003350036.1 | hypothetical protein ECSF_2046 | *Escherichia coli* SE15 |
| EES78774.1 | triosephosphate isomerase | *Ruminococcus* sp. 5_1_39BFAA |
| EFJ74438.1 | glycerophosphodiester phosphodiesterase family protein | *Escherichia coli* MS 198-1 |

TABLE 4-continued the two hundred and forty-six protein groups were identified as being differentially
abundant as compared to the non-treated control group following metaproteomics with SILAMi.

| Protein_ID | Protein_name | taxonomy |
|---|---|---|
| EFD83709.1 | universal stress family protein | *Klebsiella* sp. 1_1_55 |
| EFK02128.1 | L-asparaginase, type II | *Escherichia coli* MS 182-1 |
| EFU51004.1 | phosphoenolpyruvate carboxykinase (ATP) | *Escherichia coli* MS 153-1 |
| EFG23975.1 | methylmalonyl-CoA carboxyltransferase 12S subunit | *Veillonella* sp. 3_1_44 |
| EFK64468.1 | transporter, MotA TolQ ExbB proton channel family protein | *Parabacteroides* sp. 20_3 |
| EFJ83172.1 | arylsulfatase | *Escherichia coli* MS 69-1 |
| EEH87575.1 | oxidoreductase, short chain dehydrogenase reductase family protein | *Escherichia* sp. 3_2_53FAA |
| EFY04740.1 | methylmalonyl-CoA decarboxylase alpha subunit | *Phascolarctobacterium succinatutens* YIT 12067 |
| EHP67477.1 | galactokinase | *Escherichiac oli* 4_1_47FAA |
| EHI58078.1 | glyceraldehyde-3-phosphate dehydrogenase | *Clostridium hathewayi* WAL-18680 |
| EGB74319.1 | carbon starvation protein CstA | *Escherichia coli* MS 57-2 |
| EFJ62757.1 | threonine ammonia-lyase | *Escherichia coli* MS 200-1 |
| YP_007825311.1 | Glutamate dehydrogenase leucine dehydrogenase | butyrate-producing bacterium SS3 4 |
| EFJ73903.1 | galactose mutarotase | *Escherichia coli* MS 198-1 |
| AGJ85389.1 | threonine dehydratase | *Raoultella ornithinolytica* B6 |
| EFE22430.1 | L-asparaginase, type II | *Edwardsiella tarda* ATCC2 3685 |
| EHC27190.1 | chaperonin 1 | *Propionibacterium* sp. 5_U_42AFAA |
| EDN83951.1 | chaperonin GroL | *Bifidobacteriuma dolescentis* L2-32 |
| YP_007766843.1 | chaperonin GroL | *Bifidobacterium longum* subsp. *longum* F8 |
| EEZ21779.1 | ribosomal protein L22 | *Bacteroides* sp. 3_1_33FAA |
| EFJ96310.1 | UDP-glucose 4-epimerase | *Escherichia coli* MS 115-1 |
| EEY85226.1 | outer membrane protein 40 | *Bacteroides* sp. 2_1_33B |
| EFK20636.1 | PTS system, N-acetylglucosamine-specific IIBC component | *Escherichia coli* MS 21-1 |
| EFJ79729.1 | PTS system, N-acetylglucosamine-specific IIBC component | *Escherichia coli* MS 69-1 |
| YP_003348608.1 | glutaminyl-tRNA synthetase | *Escherichia coli* SE15 |
| EEH84887.1 | universal stress family protein | *Escherichia* sp. 3_2_53FAA |
| EDY33848.1 | ribosomal protein L13 | *Ruminococcus lactaris* ATCC 29176 |
| EGB20384.1 | ribosomal protein L13 | *Clostridium symbiosum* WAL-14673 |
| EDQ97629.1 | hypothetical protein CLOBAR 00369 | *Intestinibacter bartlettii* DSM 16795 |
| EFJ75883.1 | ABC transporter, substrate-binding protein, family 5 | *Escherichia coli* MS 198-1 |
| EFU59091.1 | Glu Leu Phe Val dehydrogenase, dimerization domain protein | *Escherichia coli* MS 16-3 |
| B6I3D0.1 | Glycine--tRNA ligase alpha subunit | *Escherichia coli* SE11 |
| EEH85049.1 | hypothetical protein ESAG_00761 | *Escherichia* sp. 3_2_53FAA |
| B6I227.1 | 50S ribosomal protein L16 | *Escherichia* coli SE11 |
| EFK74482.1 | tyrosine--tRNA ligase | *Escherichia* coli MS 78-1 |
| WP_001295080.1 | lysyl-tRNA synthetase | *Escherichia* sp. 4_1_40B |
| AFU19253.1 | chaperonin GroEL | *Actinobacillus suis* H91-0380 |
| YP_003349385.1 | 30S ribosomal protein S22 | *Escherichia coli* SE15 |
| EFV40188.1 | 2,3,4,5-tetrahydropyridine-2,6-dicarboxylate N-succinyltransferase | Enterobacteriaceae bacterium 9_2_54FAA |
| EFK88351.1 | isoleucine--tRNA ligase | *Escherichia coli* MS 146-1 |
| EFD82816.1 | 2,3,4,5-tetrahydropyridine-2,6-dicarboxylate N-succinyltransferase | *Klebsiella* sp. 1_1_55 |
| EHP65572.1 | phenylalanyl-tRNA synthetase alpha chain | *Escherichia coli* 4_1_47FAA |
| EEH89206.1 | LOW QUALITY PROTEIN: hypothetical protein ESAG_04918, partial | *Escherichia* sp. 3_2_53FAA |
| EFJ71500.1 | GMP reductase | *Escherichia coli* MS 198-1 |
| ADX45418.1 | anti-sigma H sporulation factor, LonB | *Acidovorax avenae* subsp. *avenae* ATCC 19860 |
| EGG53815.1 | putative transcriptional regulatory protein FixJ | *Parasutterella excrementihominis* YIT 11859 |
| B6I152.1 | LPS-assembly lipoprotein LptE | *Escherichia coli* SE11 |
| EFC57150.1 | hypothetical protein ENTCAN_05663 | *Enterobacter cancerogenus* ATCC 35316 |
| EKA96042.1 | adenylosuccinate synthetase | *Proteus mirabilis* WGLW6 |
| EHM49114.1 | lysine--tRNA ligase | *Yokenella regensburgei* ATCC 43003 |
| EFJ58662.1 | glutamate--tRNA ligase | *Escherichia coli* MS 200-1 |
| YP_003351947.1 | peptide ABC transporter substrate binding component | *Escherichia coli* SE15 |
| EFU57211.1 | hypothetical protein HMPREF9545_03054 | *Escherichia coli* MS 16-3 |
| EGK61283.1 | chaperone GroEL | *Enterobacter hormaechei* ATCC 49162 |
| EDU60353.1 | peptidyl-prolyl cis-trans isomerase B | *Providencia stuartii* ATCC 25827 |
| EFJ74879.1 | Dyp-type peroxidase family protein | *Escherichia coli* MS 198-1 |
| YP_003349700.1 | glucose-6-phosphate dehydrogenase | *Escherichia coli* SE15 |
| EHM47365.1 | glyceraldehyde-3-phosphate dehydrogenase, type I | *Yokenella regensburgei* ATCC 43003 |
| YP_003349494.1 | outer membrane lipoprotein | *Escherichia coli* SE15 |
| EEH72503.1 | phosphopentomutase | *Escherichia* sp. 1_1_43 |
| YP_003539075.1 | pyruvate kinase II | *Erwinia amylovora* ATCC 49946 |

TABLE 4-continued the two hundred and forty-six protein groups were identified as being differentially
abundant as compared to the non-treated control group following metaproteomics with SILAMi.

| Protein_ID | Protein_name | taxonomy |
|---|---|---|
| YP_003348183.1 | hypothetical protein ECSF_0193 | *Escherichia coli* SE15 |
| EFJ68155.1 | ATP-dependent protease HslVU, ATPase subunit | *Escherichia coli* MS 175-1 |
| YP_003348995.1 | hypothetical protein ECSF_1005 | *Escherichia coli* SE15 |
| YP_003537512.1 | molecular chaperone GroEL | *Erwinia amylovora* ATCC 49946 |
| YP_007847195.1 | glutamyl-tRNA synthetase | *Enterobacter cloacae* subsp. *cloacae* NCTC 9394 |
| EEH92664.2 | glyceraldehyde-3-phosphate dehydrogenase A | *Citrobacter* sp. 30_2 |
| EKA97512.1 | glycyl-tRNA synthetase alpha subunit | *Proteus mirabilis* WGLW6 |
| EFK92190.1 | ADP-glyceromanno-heptose 6-epimerase | *Escherichia coli* MS 146-1 |
| YP_003348413.1 | acridine efflux pump protein AcrA AltName: Full = GroEL protein;AltName: Full = Protein Cpn60;CH60_ECOSE RecName: | *Escherichia coli* SE15 |
| B6I615.1 | Full = 60 kDa chaperonin | 0 |
| YP_003537198.1 | serine acetyltransferase | *Erwinia amylovora* ATCC4 9946 |
| EFK17770.1 | co-chaperone GrpE | *Escherichia coli* MS 21-1 |
| ADN76170.1 | pyruvate kinase | *Ferrimonas balearica* DSM9 799 |
| YP_003350270.1 | PTS system enzyme I | *Escherichia coli* SE15 |
| EFP65709.1 | phosphopyruvate hydratase | *Ralstonia* sp. 5_7_47FAA |
| B3PJB3.1 | 2-phospho-D-glycerate hydro-lyase | *Cellvibrio japonicus* Ueda107 |
| EEH94022.2 | autonomous glycyl radical cofactor | *Citrobacter* sp. 30_2 |
| EEH95287.2 | aspartate-semialdehyde dehydrogenase | *Citrobacter* sp. 30_2 |
| EHP49497.1 | enolase | *Clostridium perfringens* WAL-14572 |
| EFJ73315.1 | sporulation and cell division repeat protein | *Escherichia coli* MS 198-1 |
| YP_002292075.1 | translocation protein TolB | *Escherichia coli* SE11 |
| EFU37439.1 | hexose kinase, 1-phosphofructokinase family | *Escherichia coli* MS 85-1 |
| B6I4S5.1 | Heat shock protein HslV | *Escherichia coli* SE11 |
| EFU37381.1 | glyceraldehyde-3-phosphate dehydrogenase, type I | *Escherichia coli* MS 85-1 |
| YP_003349138.1 | putative PTS system enzyme I | *Escherichia coli* SE15 |
| EGJ08498.1 | 6-phosphofructokinase | *Shigella* sp. D9 |
| EJZ47828.1 | fructose-bisphosphate aldolase class 1 | *Escherichia* sp. 1_1_43 |
| EFK73994.1 | NAD(P)H:quinone oxidoreductase, type IV | *Escherichia coli* MS 78-1 |
| YP_003348173.1 | methionine aminopeptidase | *Escherichia coli* SE15 |
| WP_018592092.1 | hypothetical protein | *Terrisporobacter glycolicus* |
| EDO60098.1 | formate C-acetyltransferase | *Clostridium leptum* DSM7 53 |
| WP_024039107.1 | Formate acetyltransferase | *Clostridium butyricum* |
| EGU99618.1 | 2,3-bisphosphoglycerate-independent phosphoglycerate mutase | *Escherichia coli* MS 79-10 |
| EFU56329.1 | 2,3-bisphosphoglycerate-independent phosphoglycerate mutase | *Escherichia coli* MS 16-3 |
| B6I2X8.1 | Fe S biogenesis protein NfuA | *Escherichia coli* SE11 |
| EEH87714.1 | autonomous glycyl radical cofactor | *Escherichia* sp. 3_2_53FAA |
| A6VUU9.1 | 2-phospho-D-glycerate hydro-lyase | *Marinomonas* sp. MWYL1 |
| YP_003348538.1 | alkyl hydroperoxide reductase subunit F | *Escherichia coli* SE15 |
| YP_002291949.1 | alkyl hydroperoxide reductase subunit F | *Escherichia coli* SE11 |
| EFJ56595.1 | stringent starvation protein A | *Escherichia coli* MS 185-1 |
| YP_003348537.1 | alkyl hydroperoxide reductase subunit C | *Escherichia coli* SE15 |
| EFK73356.1 | chaperonin GroS | *Escherichia coli* MS 78-1 |
| WP_009008039.1 | autonomous glycyl radical cofactor GrcA | *Shigella* sp. D9 |
| EFK71210.1 | glucose-6-phosphate isomerase | *Escherichia coli* MS 78-1 |
| AGJ88568.1 | ADP-L-glycero-D-mannoheptose-6-epimerase | *Raoultella ornithinolytica* B6 |
| EKB82759.1 | chaperonin | *Klebsiella pneumoniae*s ubsp. *pneumoniae* WGLW5 |
| YP_003348095.1 | cell division protein FtsZ | *Escherichia coli* SE15 |
| YP_002291773.1 | heat shock protein 90 | *Escherichia coli* SE11 |
| EFK25863.1 | deoxyribose-phosphate aldolase | *Escherichia coli* MS 187-1 |
| EFU57607.1 | deoxyribose-phosphate aldolase | *Escherichia coli* MS 16-3 |
| EFJ62792.1 | hypothetical protein HMPREF9553_01102 | *Escherichia coli* MS 200-1 |
| YP_003350475.1 | autoinducer-2 production protein | *Escherichia coli* SE15 |
| EFU58344.1 | peptidyl-prolyl cis-trans isomerase B | *Escherichia coli* MS 16-3 |
| EGF14772.1 | formate acetyltransferase | *Haemophilus aegyptius* ATCC 11116 |
| YP_003348814.1 | formate acetyltransferase 1 | *Escherichia coli* SE15 |
| EFE22433.1 | formate C-acetyltransferase | *Edwardsiella tarda* ATCC 23685 |
| EGU97855.1 | formate acetyltransferase | *Escherichia coli* MS 79-10 |
| EFK20865.1 | phosphoserine transaminase | *Escherichia coli* MS 21-1 |
| A6VZ92.1 | Phosphohydroxythreonine aminotransferase | *Marinomonas* sp. MWYL1 |
| EFD85361.1 | formate C-acetyltransferase | *Klebsiella* sp. 1_1_55 |
| EFJ53806.1 | rhodanese-like protein | *Escherichia coli* MS 185-1 |
| EFK44911.1 | formate C-acetyltransferase | *Escherichia coli* MS 119-7 |
| YP_004220428.1 | formate acetyltransferase | *Bifidobacterium longum* subsp. *longum* JCM 1217 |
| AGJ89504.1 | S-ribosylhomocysteinase | *Raoultella ornithinolytica* B6 |
| YP_003349716.1 | aspartyl-tRNA synthetase | *Escherichia coli* SE15 |
| EEH86836.1 | aspartate--tRNA ligase | *Escherichia* sp. 3_2_53FAA |
| EDP16360.1 | hypothetical protein CLOBOL_03126 | *Clostridium bolteae* ATCC BAA-613 |
| EFR46519.1 | chaperone protein ClpB | *Helicobacter cinaedi* CCUG 18818 |

TABLE 4-continued the two hundred and forty-six protein groups were identified as being differentially
abundant as compared to the non-treated control group following metaproteomics with SILAMi.

| Protein_ID | Protein_name | taxonomy |
| --- | --- | --- |
| EFK89002.1 | glycerol-3-phosphate dehydrogenase, anaerobic, C subunit | *Escherichia coli* MS 146-1 |
| EFK00860.1 | beta-aspartyl peptidase | *Escherichia coli* MS 182-1 |
| EFO55869.1 | chaperone protein DnaK | *Escherichia coli* MS 145-7 |
| YP_003350137.1 | hypothetical protein ECSF_2147 | *Escherichia coli* SE15 |
| YP_003351949.1 | truncated formate dehydrogenase H, partial | *Escherichia coli* SE15 |
| EGU96599.1 | ATP-dependent chaperone protein ClpB | *Escherichia coli* MS 79-10 |
| EFE53197.1 | methionine adenosyltransferase | *Providencia rettgeri* DSM 1131 |
| YP_003537739.1 | chaperone protein | *Erwinia amylovora* ATCC 49946 |
| EEH84693.1 | outer membrane protein X | *Escherichia* sp. 3_2_53FAA |
| EFU58863.1 | pyrroline-5-carboxylate reductase | *Escherichia coli* MS 16-3 |
| EFK20818.1 | curved DNA-binding protein | *Escherichia coli* MS 21-1 |
| EFD82978.1 | chaperone protein DnaK | *Klebsiella* sp. 1_1_55 |
| YP_003351331.1 | putative lipoprotein | *Escherichia coli* SE15 |
| EEH85525.1 | TIGR00156 family protein | *Escherichia* sp. 3_2_53FAA |
| EFO56144.1 | outer membrane protein slp | *Escherichia coli* MS 145-7 |
| EHP49037.1 | chaperone ClpB | *Clostridium perfringens* WAL-14572 |
| EFB70971.1 | chaperone protein DnaK | *Providencia rustigianii* DSM 4541 |
| EEZ20102.1 | hypothetical protein HMPREF0105_3492 | *Bacteroides* sp. 3_1_33FAA |
| EFJ65716.1 | putative protein HdeB | *Escherichia coli* MS 175-1 |
| EFU51921.1 | DNA protection during starvation protein | *Escherichia coli* MS 153-1 |
| EJZ49312.1 | N-acetylglucosamine-6-phosphate deacetylase | *Escherichia* sp. 1_1_43 |
| EFU58593.1 | DNA protection during starvation protein | *Escherichia coli* MS 16-3 |
| EFO58101.1 | N-acetylglucosamine-6-phosphate deacetylase | *Escherichia coli* MS 145-7 |
| YP_003349426.1 | hypothetical protein ECSF_1436 | *Escherichia coli* SE15 |
| EFU51394.1 | glucosamine-6-phosphate deaminase | *Escherichia coli* MS 153-1 |
| EEH70955.1 | aspartate-ammonia ligase | *Escherichia* sp. 1_1_43 |
| YP_003349391.1 | amino acid antiporter | *Escherichia coli* SE15 |
| EFK92597.1 | oxygen-insensitive NAD(P)H nitroreductase | *Escherichia coli* MS 146-1 |
| EFK24351.1 | aminotransferase AlaT | *Escherichia coli* MS 187-1 |
| EFK90487.1 | glutamate decarboxylase | *Escherichia coli* MS 146-1 |
| YP_003351335.1 | glutamate decarboxylase | *Escherichia coli* SE15 |
| EFC55519.1 | asparagine synthase (glutamine-hydrolyzing) | *Enterobacter cancerogenus* ATCC 35316 |
| EFK50572.1 | asparagine synthase (glutamine-hydrolyzing) | *Escherichia coli* MS 107-1 |
| EFR55608.1 | ribosomal protein S10 | *Bacteroides fragilis* 3_1_12 |
| EFR55609.1 | 50S ribosomal protein L3 | *Bacteroides fragilis* 3_1_12 |
| EFK61943.1 | SusD family protein | *Parabacteroides* sp. 20_3 |
| EBA38760.1 | ribosomal protein S20 | *Collinsella aerofaciens* ATCC 25986 |
| EGB75313.1 | indole-3-glycerol phosphate synthase | *Escherichia coli* MS 57-2 |
| EFK61740.1 | Tat pathway signal sequence domain protein | *Parabacteroides* sp. 20_3 |
| EET16977.1 | phosphoglucomutase | *Bacteroides* sp. 4_3_47FAA |

Unique metaproteome patterns were observed in response to the different monosaccharide treatments (FIG. 3C). The monosaccharide fucose showed the smallest effect on the metaproteome, however cluster 206, mainly consisting of fucose utilization-related proteins, was increased only in the fucose-treated microbiota (FIG. 3C). Moreover, all of the six quantified fucose utilizing proteins in the fucose utilization pathway were increased upon the supplementation of fucose (FIG. 3D) [12]. On the other hand, GlcNAc resulted in the most dramatic alterations of the metaproteome with significant increase of GlcNAc degrading proteins (FIG. 3A-C), which produce fructose 6-phosphate and NH3. The latter may be used for asparagine synthesis since asparagine synthase was also significantly increased (FIG. 3D).

As a result, it is shown that use of the heavy-labelled standard obtained via SILAMi may be used to assess changes in a microbiome as a result of a given compound. More specifically, this approach allows for identification of specific pathways and metabolic processes which may be altered in a treated microbiome sample. This data could be used by one of skill in the art to determine who changes in composition effect function as well as identify pathways effected in disease and by drug and chemical treatment. It will be understood that such compounds may include xenobiotics, but also drugs, chemicals, therapeutic agents, toxins, poisons, beverages, food additives, cosmetics, cosmetic ingredients, packaging materials, pesticides, herbicides, consumer products. A skilled person recognizes that a given microbiome is very sensitive to change, and therefore such a compound may have an impact upon the microbiome. Such an impact is now quantifiable as a result of the heavy-labelled standard developed using the SILAMi technique.

Taken together, a fast and cost-effective approach is provided, namely SILAMi, to perform accurate and large-scale quantitative metaproteomic studies on the microbiota. Moreover, it was successfully applied to screen and evaluate the effects of different compounds on human microbiota. More interestingly, new insights on the interactions between drug, microbe and host may be acquired through experiments benefiting from the heavy-labelled standard obtained with SILAMi. Thus, the application of SILAMi can help to improve the accuracy of metaproteomics, thereby largely promoting its application in studying the microbiota in the context of health and disease. It will be understood that such study in the context and disease may include determining for a given patient if the disease is in remission or if the disease is worsening in severity. The study may also involve determining if a patient is responding to a given treatment, or even determining which treatment should be given for a specific patient. Furthermore, diagnosis of disease is also possible with SILAMi. It is known in that changes in health and disease often yield a change in the microbiota of the patient. These changes, in particular in depth metaproteomic changes, can now be quantified and analyzed as a result of the heavy-labelled standard obtained using SILAMi.

Figure 8:
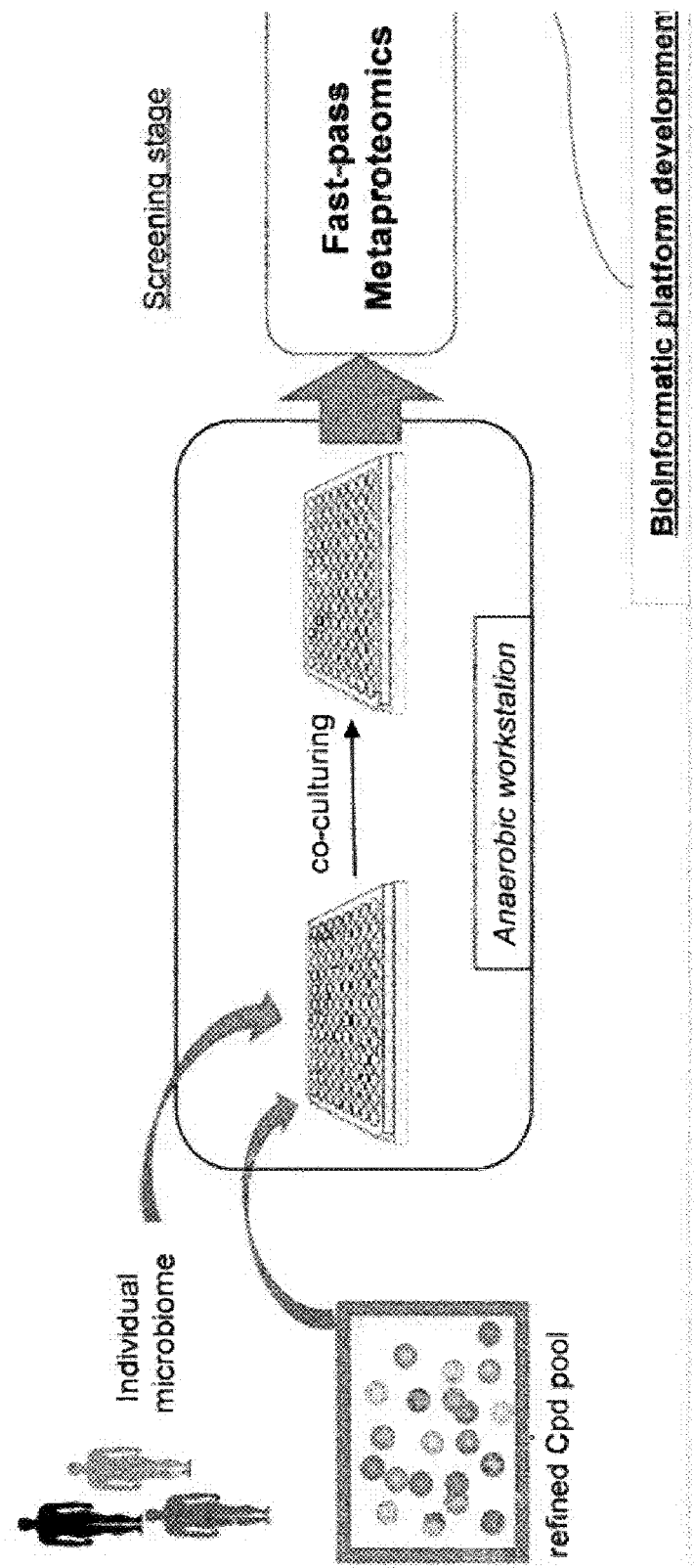
FIG. 8 illustrates an exemplary workflow of RapidAIM. Rapid Analysis of Individual Microbiota (RapidAIM) through fast-pass metaproteomics for rapid screening and in-depth metaproteomics/metagenomics for mechanism interpretation. The workflow includes high-performance, easy-to-use software platforms for rapidly identifying positive hits and providing functional insights into microbiome changes.
Figure 8:
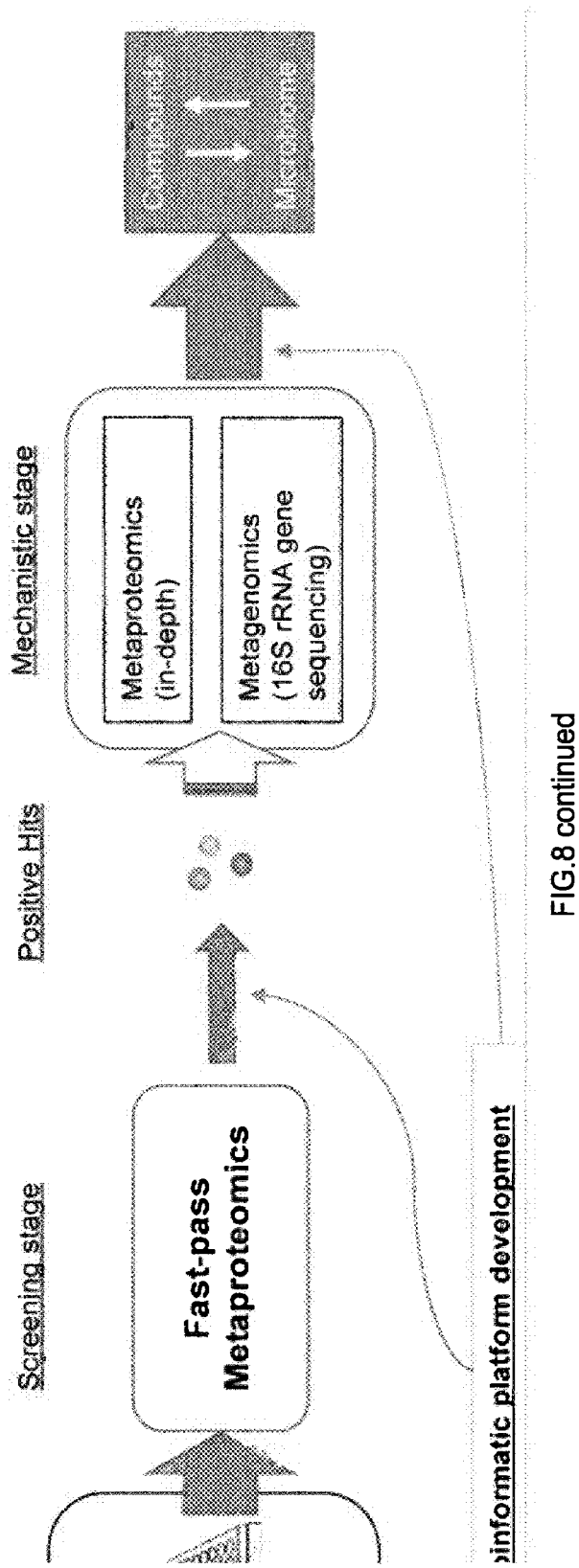
Figure 8:
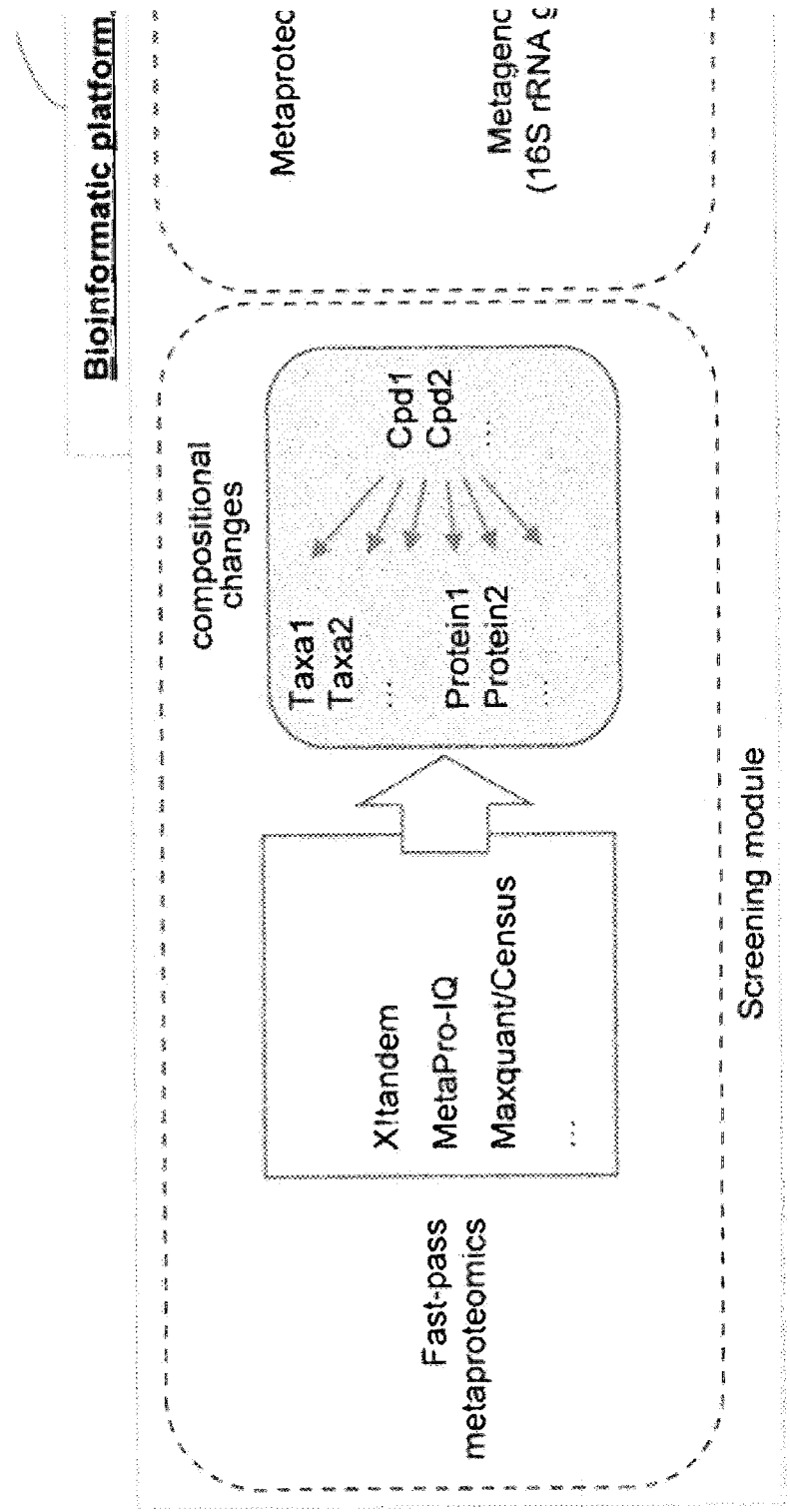
Figure 8:
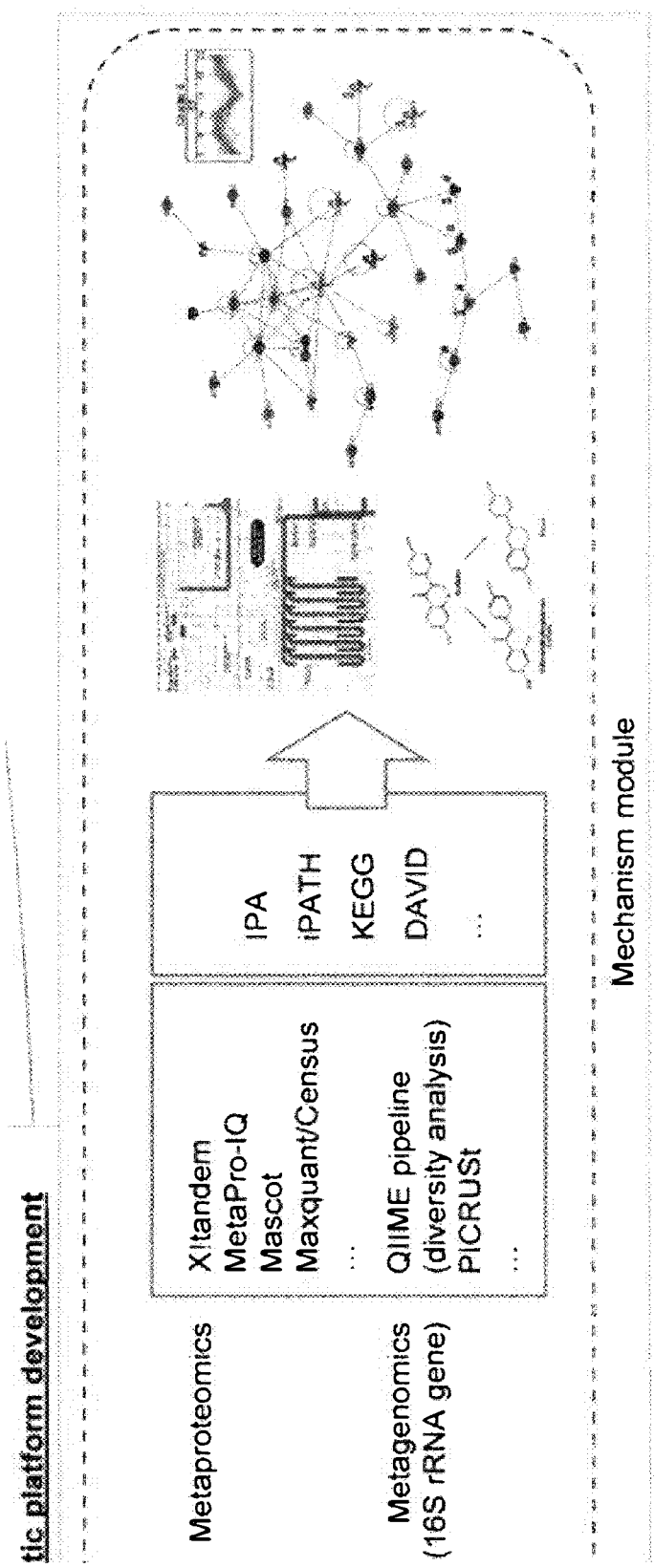
Figure 9:
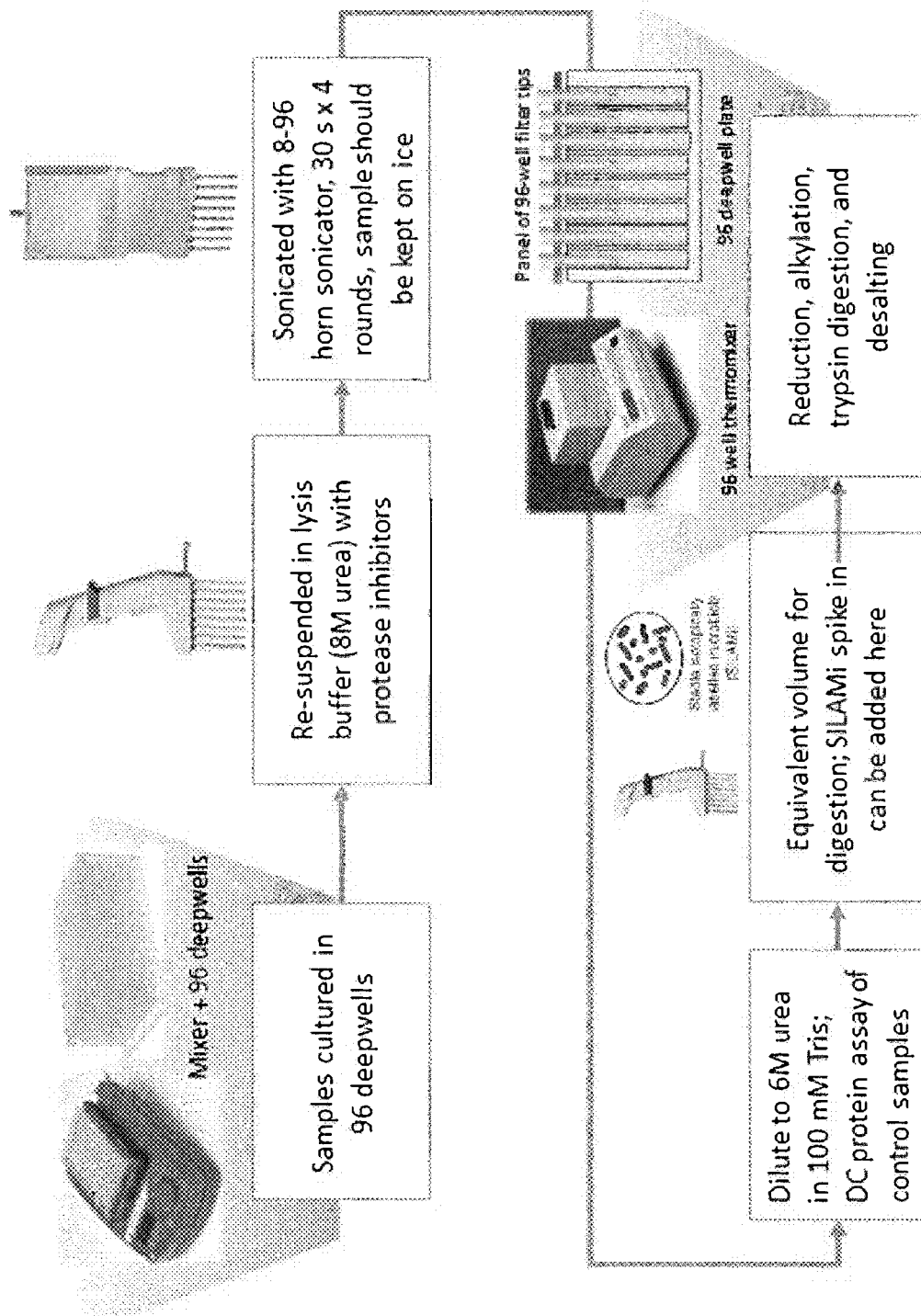
FIG. 9 illustrates an exemplary 96-well-based culturing and metaproteomic experimental workflow for the RapidAIM assay, which can be used to assess any set of microbiome samples, including those from multiple individuals, in a multi-well format. Briefly, the microbiome samples cultured in 96 deepwells are washed with PBS and re-suspended in urea lysis buffer. Then the samples are sonicated with a multi-channel sonicator for cell lysis. The protein concentrations of control samples (in triplicates) are tested and all samples will be digested in a volume equivalent to 100 μg proteins in the control. 1:1 protein content of SILAMi reference can be spiked-in in this step (but spiking with the SILAMi reference is not required). After reduction and alkylation, the proteins are digested by trypsin and are desalted. This workflow allows for accurate and reproducible high throughput metaproteomic analysis in a multi-well. This provides a screening platform that is capable of assessing changes due to disease, drug treatment or any other manipulation or treatment of the microbiome samples while in culture. Furthermore, this allow for the simultaneous culture and assessment of the microbiome samples from multiple individuals in a multi-well format, allowing for high-throughput screening in a compact and time-efficient manner.

Example 2: RapidAIM, a High Throughput Screening Platform to Assess the Effect of Drugs Reference is now made to RapidAIM, an experimental and computational framework to rapidly assay an individual's microbiome (called RapidAIM), a platform to assess the effects of compounds including but not limited to drugs on the microbiome and drug metabolism is described. The use of RapidAIM to validate the platform for compounds, specifically, in this example, those used in IBD, is described (FIGS. 8, 9). Briefly, RapidAIM consists of panel of microbiomes derived from multiple individuals that are treated with selected compounds and screened in a multi-well format; This approach allows for rapid classification of compounds that have no affect or affect the microbiota composition (biota-affectors), or compounds that are affected by the microbiome (biota-altered) using metagenomic ($^{16}$S-based sequencing), and/or fast-pass metaproteomics, and/or metabolomics assessment of the microbiome's metabolic activities on the compound; Optionally, the RapidAIM platform will be utilized to gain mechanistic insights on these compounds in combination with functional metagenomics, metatranscriptomics and in depth metaproteomics. It will be appreciated that certain steps of the RapidAIM can be performed separately. Finally, this bioinformatics platform can be used to rapidly guide the selection of positive hit compounds based on the metaOMICS analyses of an individual's microbiome or broad screening of many microbiomes. Currently, no technology exists to rapidly assay individual microbiome, particularly with respect to metaproteomics. The RapidAIM project is transformative to the pharmaceutical and biotechnology development and microbiology field, as it allows for the rapid screening of candidate drugs against human microbiome before the drugs are commercialized, to screen current drugs for potential adverse microbiome effects, to stratify patients based on their response to drug treatment, and to screen compounds that would have efficacy across a wider population.

In another embodiment, RapidAIM can be used to screen a panel of microbiomes derived from IBD and control patients in multi-well plates against selected xenobiotics. However, it will be understood that RapidAIM may also be used in the context of selected therapeutics, amino acids, and dietary supplements, etc. Assessment of the changes in the metaproteome upon treatment with any such compounds in the microbiota of healthy individuals or those associated with a disease other than inflammatory bowel disease may be similarly performed without departing from the present teachings. Biota-affectors can be selected by metagenomic ($^{16}$S-based sequencing) analysis of microbial composition changes and fast-pass metaproteomics to identify impacts on the top 1,500 most abundant proteins. Biota-altered compounds can be identified by metabolomics. Each multi-well plate takes approximately 2 days for screening and can identify compounds that either target specific microbes or group of microbes and/or their metabolic activities. Furthermore, this screening can be done to determine the effect of any compound upon the microbiome. The assay can be repeated on a reduced pool of compounds to generate functional metagenomics, metatranscriptomics and more in-depth metaproteomics (4000-5000 proteins/sample). A modeling algorithm can be used to rapidly guide selection of compounds based on the metaOMICS analyses, and pathway databases.

Developing RapidAIM in a multi-well plate format: microbiota can be inoculated and grown in culture media. Assays, performed in any multiwall format (e.g. 6 well to 96 well plate formats, or any other type of format, for example, using tubes) and can be titrated, examining at each stage whether the yield per well provides sufficient material for downstream analyses. The analysis can be performed using a workflow for metaproteome as described in Zhang et al. "MetaPro-IQ: a universal metaproteomic approach to studying human and mouse gut microbiota", Microbiome, 2016 Jun. 24:4(1):31, doi: 10.1186/s40168-016-0176-z. The workflow uses the close-to-complete human or mouse gut microbial gene catalog as a database and uses an iterative database search strategy. An example of a high-through put experimental workflow for the RapidAIM has been established based on a 96-well format (FIG. 9). This workflow includes, (A) 96-well based microbiome culturing, and (B) 96-well based metaproteomics analysis.

As shown in FIG. 9, one of the steps in the workflow describes how "the SILAMi spike in can be added here", where the SILAMi spike may be optionally added. The preparation of the "SILAMi spike" or the "SILAMi Reference Standard" can be prepared as described herein. Alternatively, a representative superSILAMi standard for quantitative metaproteomics can be used. To prepare a superSILAMi standard, multiple SILAMi reference samples can be combined using strategic additions to the culture media and samples from many individuals. The superSILAMi reference can be used as a comprehensive quantitative spike-in for diverse samples.

The performance of RapidAIM may also involve parameter setting for time in order to measure (i) microbiota changes and (ii) generation of drug metabolites. These can be guided for example by current literature including from in vitro liver system drug metabolism tests [13]. Briefly, microbiota can be inoculated and grown in basal culture media with or without compounds for different times (ranging from 30 min to 24 hrs), and samples collected for analyses.

The performance of RapidAIM may also involve parameter setting for the dosage of each compound in the pool which can be tested and pre-determined using the clinical dosage or reported concentrations for culturing as guidance. Microbiota from multiple individuals (including both male and female) can be used to negate inter-individual variability of intestinal microbiota.

Figure 10A:
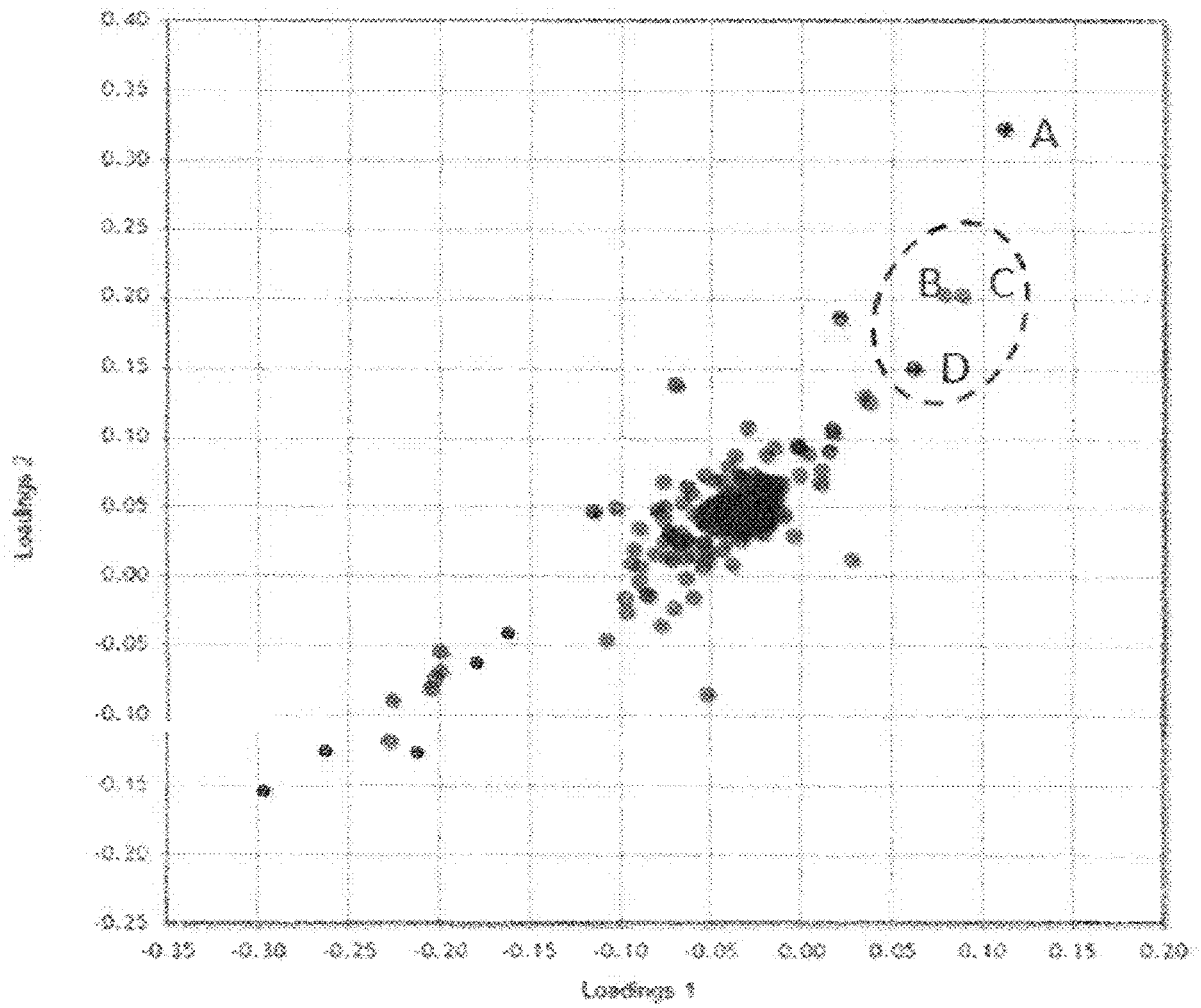
FIG. 10A shows the results from the loadings plot of a principal component analysis (PCA) with all bacterial species.
Figure 10B:
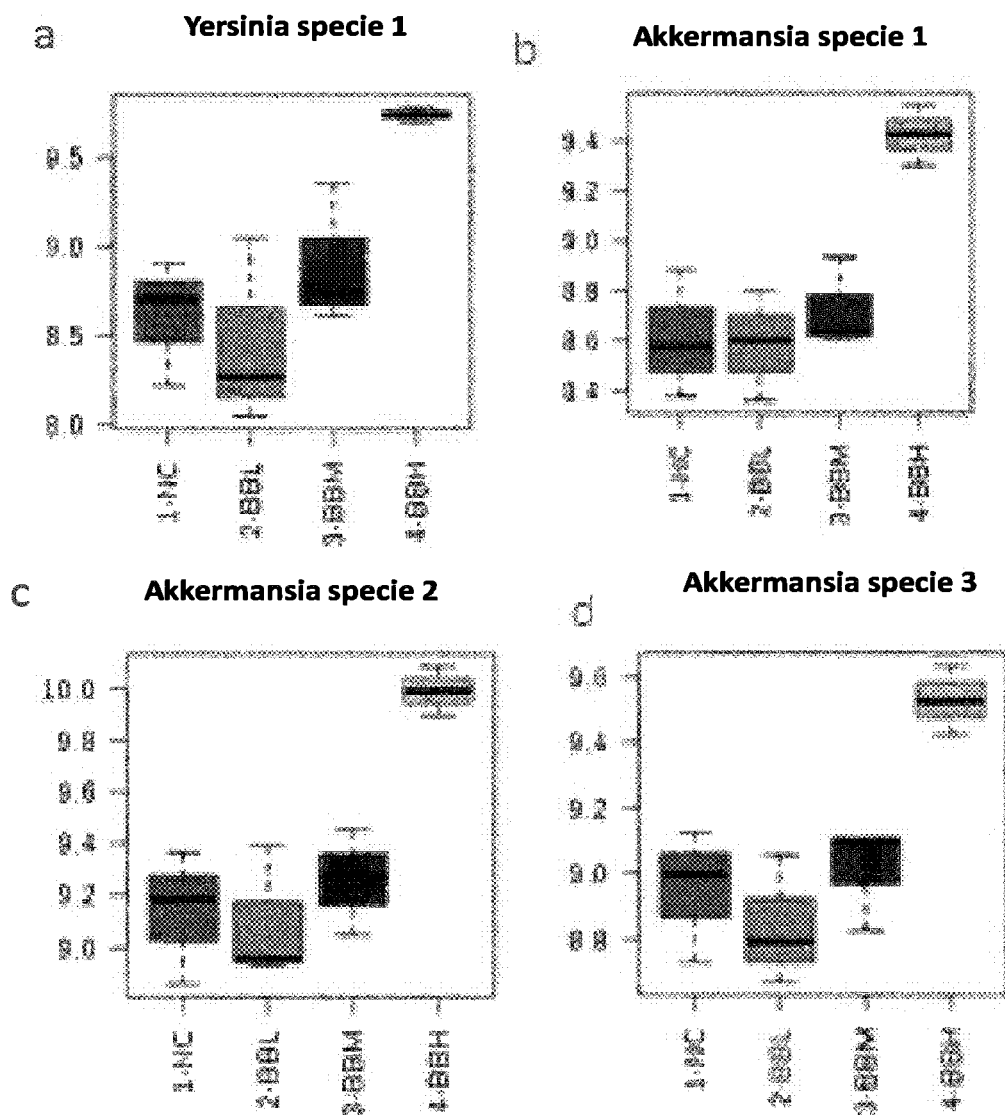
FIG. 10B shows that the abundances of the species originating from the *Akkermansia* genus (identified in FIG. 10B as *Akkermansia* species 1, *Akkermansia* species 2 and *Akkermansia* species 3) were significantly increased when treated with high concentration of Berberine. *Akkermansia* spp has been reported to be beneficial bacterial in the gut microbiome, which has been shown in other literatures to be increased by another antidiabetic drug, Metformin. It will be understood that while microbiota samples were treated with Berberine, any compound could be used in this screening platform to treat the microbiome samples and the subsequent effect on microbiome protein expression assessed with a system to perform functional and quantitative analysis of the samples.

As an example, RapidAIM was used to assay an individual a microbiome treated with a high, medium or low dose of berberine compared to the sample cultured without drug treatment (FIG. 10). The taxonomic composition at the species level were quantified in each of the cultured microbiome sample on the MetaLab bioinformatics platform. FIG. 10A shows the results from the loadings plot of a principal component analysis (PCA) with all bacterial species. FIG. 10B shows that the abundances of the species originating from the *Akkermansia* genus (identified in FIG. 10B as *Akkermansia* species 1, *Akkermansia* species 2 and *Akkermansia* species 3) were significantly increased when treated with high concentration of Berberine. *Akkermansia* spp has been reported to be beneficial bacterial in the gut microbiome, which has been shown to be increased by another antidiabetic drug, Metformin.

The description of the present invention has been presented for purposes of illustration but is not intended to be exhaustive or limited to the disclosed embodiments. Many modifications and variations will be apparent to those of ordinary skill in the art.

REFERENCES

1. Qin, J., et al. Nature, 2010. 464 (7285), 59-65.
2. Clemente, J. C., et al. Cell, 2012. 148 (6), 1258-70.
3. Kelly, C. P. N Engl J Med, 2013. 368 (5), 474-5.
4. Verberkmoes, N. C., et al. ISME J, 2009. 3 (2), 179-89.
5. Juste, C., et al. Gut, 2014. 63 (10), 1566-77.
6. Jagtap, P., et al. J Proteomics, 2013. 13, 1352-1357.
7. Ong, S. E., et al. Mol Cell Proteomics, 2002. 1 (5), 376-86.
8. Krijgsveld, J., et al. Nat Biotechnol, 2003. 21 (8), 927-31.
9. Mueller, R. S., et al. Environ Microbiol, 2011. 13, 2279-2292.
10. Park, S. K., et al. Nat Methods, 2008. 5 (4), 319-22.
11. Mesuere, B., et al. J Proteome Res, 2012. 11 (12), 5773-80.
12. Stahl, M., et al. Proc Natl Acad Sci USA, 2011. 108 (17), 7194-9.
13. Zhong, S. et al. Drug Metab Dispos, 2015.

What is claimed is:

1. A method of high throughput screening of multiple microbiota samples from a human subject, soil, or animal for metaproteomic analysis of said samples comprising:
providing proteome extracts from a plurality of microbiota samples from one or more human subjects, soil, or animals in culture;
spiking said proteome extracts with an isotope-labelled standard, which comprises a proteome of microbiota from a given human, soil, or animal microbiota sample labelled with an isotope by culturing said microbiota from a given human, soil, or animal microbiota in an isotope enriched medium;
performing a pre-screening using a metaproteomic analysis to identify changes in microbiomes of said plurality of microbiota samples;
selecting said microbiomes exhibiting changes; and
analyzing the selected microbiomes to characterize the changes.

2. The method of claim 1, wherein said analyzing comprises using a microbial gene catalog of a given subject type and an iterative database search strategy.

3. The method of claim 2, wherein said microbial gene catalog of a given subject type is a microbial gene catalog of an animal or human.

4. The method of claim 1, wherein said analyzing comprises performing a metaproteomic analysis combined with a metagenomic analysis.

5. The method of claim 1, wherein said spiking comprises adding sufficient isotope-labelled standard to reach a 1:1 protein mass ratio with the protein contained in said proteome extracts from the plurality of microbiota samples.

6. The method of claim 1, wherein the plurality of microbiota samples are from one or more human subjects or animals, and wherein the method further comprises assessing the results of said analysis of the selected microbiomes to perform at least one of:
disease diagnosis in a target human subject or an animal;
assessing treatment response in a target human subject or an animal;
assessing remission in a human subject or an animal receiving treatment;
screening for xenobiotic effects on a microbiome of a target human subject or an animal;
screening for effects of a compound on a microbiome of a target human subject or an animal, wherein said compound is one of a food, a drug, a chemical, a therapeutic agent, a toxin, a poison, a beverage, a food additive, a cosmetic, a cosmetic ingredient, packaging material, a pesticide, a herbicide, a consumer product; and
screening a microbiome to identify the responsiveness of a human subject or an animal to a therapy or treatment.

7. The method of claim 1, wherein said isotope-labelled standard comprises labelled proteins representative of a metaproteome from the given human, soil, or animal microbiota sample and having at least 90% average heavy isotopic enrichment rate.

8. The method of claim 7, wherein the given human microbiota sample is from an intestinal microbiota.

9. The method of claim 1, wherein said isotope-labelled standard is taxon-specific for at least about 50% of the microbe populations present in the plurality of microbiota samples from the one or more human subjects, soil, or animals.

10. The method of claim 1, wherein said isotope-labelled standard is taxon-specific for at least about 85% of the microbe populations present in the plurality of microbiota samples from the one or more human subjects, soil, or animals.

11. The method of claim 1, wherein the plurality of microbiota samples from the one or more human subjects are from an intestinal microbiota, a vaginal microbiota, an oral microbiota, a cutis microbiota, a bladder microbiota, a kidney microbiota, a lung microbiota, an eye microbiota, a breast microbiota, a penile microbiota, or any combination thereof.

12. The method of claim 1, wherein the isotope comprises a stable isotope, a radioactive isotope, or both.

13. The method of claim 12, wherein the isotope comprises $^{13}C$, $^{14}C$, $^{15}N$, $^{32}S$, $^{35}S$, $^{32}P$, deuterium, or any combination thereof.

* * * * *